(12) United States Patent
Nielsen et al.

(10) Patent No.: US 8,232,087 B2
(45) Date of Patent: Jul. 31, 2012

(54) SUBTILASES

(75) Inventors: Preben Nielsen, Horsholm (DK); Poul Erik Pedersen, Soborg (DK); Helle Outtrup, Skovhaven (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/023,626

(22) Filed: Feb. 9, 2011

(65) Prior Publication Data

US 2011/0130319 A1    Jun. 2, 2011

Related U.S. Application Data

(62) Division of application No. 12/879,156, filed on Sep. 10, 2010, now Pat. No. 7,910,349, which is a division of application No. 11/575,551, filed as application No. PCT/DK2005/000597 on Sep. 21, 2005, now Pat. No. 7,816,115.

(60) Provisional application No. 60/611,720, filed on Sep. 21, 2004.

(30) Foreign Application Priority Data

Sep. 21, 2004   (DK) ................. 2004 01429

(51) Int. Cl.
*C12N 9/54*     (2006.01)
*C12N 15/57*    (2006.01)
*C12N 15/62*    (2006.01)
*C12N 15/74*    (2006.01)
*C12N 15/75*    (2006.01)
*C11D 3/386*    (2006.01)

(52) U.S. Cl. ... 435/221; 435/69.1; 435/69.7; 435/252.3; 435/252.31; 435/320.1; 510/300; 536/23.2

(58) Field of Classification Search ................ None
See application file for complete search history.

(56) References Cited

U.S. PATENT DOCUMENTS

| | | | |
|---|---|---|---|
| 5,891,701 A | 4/1999 | Sloma et al. |
| 6,303,752 B1 | 10/2001 | Olsen et al. |
| 6,416,756 B1 | 7/2002 | Olsen et al. |
| 6,638,526 B1 | 10/2003 | Deussen et al. |
| 6,803,222 B2 | 10/2004 | Hatada et al. |
| 7,101,698 B2 | 9/2006 | Sato et al. |
| 7,163,807 B2 | 1/2007 | Sato et al. |
| 7,371,839 B2 | 5/2008 | Hatada et al. |
| 7,405,271 B2 | 7/2008 | Sato et al. |
| 7,429,642 B2 | 9/2008 | Okuda et al. |

(Continued)

FOREIGN PATENT DOCUMENTS

EP        1290 233         5/2002
WO    WO 2004/083362 A2   9/2004

OTHER PUBLICATIONS

Gupta et al, Applied Microbiology Biotechnology, vol. 59 No. (1), pp. 15-32 (2002).

(Continued)

*Primary Examiner* — Manjunath Rao
*Assistant Examiner* — William W Moore
(74) *Attorney, Agent, or Firm* — Kristin J. McNamara

(57) ABSTRACT

The present invention relates to novel JP170 like subtilases from wild-type bacteria, hybrids thereof and to methods of construction and production of these proteases. Further, the present invention relates to use of the claimed subtilases in detergents, such as a laundry or an automatic dishwashing detergent.

17 Claims, 2 Drawing Sheets

Phylogenetic tree

U.S. PATENT DOCUMENTS

| | | |
|---|---|---|
| 7,473,544 B2 | 1/2009 | Okuda et al. |
| 7,811,979 B2 * | 10/2010 | Nielsen et al. ............... 510/393 |
| 7,816,115 B2 * | 10/2010 | Nielsen et al. ............... 435/221 |
| 7,910,349 B2 * | 3/2011 | Nielsen et al. ............... 435/221 |
| 2004/0002432 A1 | 1/2004 | Okuda et al. |
| 2007/0015240 A1 | 1/2007 | Svendsen et al. |
| 2008/0187958 A1 | 8/2008 | Nielsen et al. |
| 2010/0311635 A1 * | 12/2010 | Nielsen et al. ............... 510/226 |

OTHER PUBLICATIONS

Maurer, Current Opinion in Biotechnology, vol. 15, No. (4), pp. 330-334 (2004).

Saeki et al, Biochemical and Biophysical Research Communications vol. 279, No. (2), pp. 313-319—(2000).

* cited by examiner

Phylogenetic tree

|  | D6 | JP170 | JT169 | KAO-A1 | KSM-KP43 | KSM-KP9860 | KSM-KP9865 | JP170/PD456 | JP170/JT169 | JP170/JP75 | JP170/JP40 | PD456 | ProtY |
|---|---|---|---|---|---|---|---|---|---|---|---|---|---|
| JP170 | 88,9 | | | | | | | | | | | | |
| JT169 | 87,3 | 92,2 | | | | | | | | | | | |
| KAO-A1 | 88,5 | 91,9 | 94 | | | | | | | | | | |
| KSM-KP43 | 87,5 | 93,5 | 93,3 | 93,5 | | | | | | | | | |
| KSM-KP9860 | 88,2 | 93,1 | 91,7 | 92,4 | 96,5 | | | | | | | | |
| KSM-KP9865 | 87,8 | 93,8 | 93,5 | 93,8 | 99,8 | 96,8 | | | | | | | |
| JP170/PD456 | 87,1 | 92,6 | 93,8 | 92,4 | 92,9 | 92,2 | 93,1 | | | | | | |
| JP170/JT169 | 87,8 | 94 | 97,9 | 93,1 | 93,1 | 91,2 | 93,3 | 95,9 | | | | | |
| JP170/AMRK133 | 88,2 | 94,7 | 94,5 | 93,5 | 93,1 | 93,5 | 93,3 | 97,5 | 96,5 | | | | |
| JP170/JP75 | 88,9 | 94 | 94,9 | 93,1 | 92,6 | 92,6 | 92,9 | 97 | 97 | | | | |
| JP170/JP40 | 88,7 | 94 | 94,7 | 93,8 | 92,9 | 92,9 | 93,1 | 97,2 | 96,8 | 99,3 | | | |
| PD456 | 87,1 | 91,5 | 95,4 | 94,2 | 93,3 | 92,9 | 93,5 | 97,7 | 94,5 | 95,6 | 95,9 | | |
| ProtY | 98,8 | 88,7 | 87,1 | 88 | 87,5 | 88,2 | 87,8 | 87,1 | 87,5 | 88,9 | 88,7 | 86,6 | |
| SD521 | 99,3 | 89,1 | 87,5 | 88,7 | 88 | 88,7 | 88,2 | 87,5 | 88 | 89,4 | 89,1 | 87,5 | 99,1 |

Fig. 2

Identity matrix

SEQUENCE LISTING

<160> NUMBER OF SEQ ID NOS: 34

<210> SEQ ID NO 1
<211> LENGTH: 1305
<212> TYPE: DNA
<213> ORGANISM: Artificial sequence
<220> FEATURE:
<223> OTHER INFORMATION: Strain JT169
<220> FEATURE:
<221> NAME/KEY: CDS
<222> LOCATION: (1)..(1305)

<400> SEQUENCE: 1

```
aat gat gta gcg aga ggg att gtt aaa gcc gat gtt gcc caa agc agt      48
Asn Asp Val Ala Arg Gly Ile Val Lys Ala Asp Val Ala Gln Ser Ser
1               5                   10                  15 tat ggg tta tat ggg caa ggt caa aca gtt gct gta gca gat act ggt      96
Tyr Gly Leu Tyr Gly Gln Gly Gln Thr Val Ala Val Ala Asp Thr Gly
                20                  25                  30 ctt gat acc ggg cgt aac gac agc tcc atg cat gaa gct ttc cgc gga     144
Leu Asp Thr Gly Arg Asn Asp Ser Ser Met His Glu Ala Phe Arg Gly
            35                  40                  45 aaa atc act gcg ttg tat gcc tta gga aga acc aat aat tcc aac gat     192
Lys Ile Thr Ala Leu Tyr Ala Leu Gly Arg Thr Asn Asn Ser Asn Asp
        50                  55                  60 cca aat ggt cac gga acg cac gtt gcc gga tct gtt ctt gga aac gga     240
Pro Asn Gly His Gly Thr His Val Ala Gly Ser Val Leu Gly Asn Gly
65                  70                  75                  80 aca agc aat aaa gga atg gcg cca caa gca aat cta gta ttt caa tcc     288
Thr Ser Asn Lys Gly Met Ala Pro Gln Ala Asn Leu Val Phe Gln Ser
                85                  90                  95 atc atg gat agc ggc ggt gga ttg ggc ggc ctt cca tcc aac ctg agc     336
Ile Met Asp Ser Gly Gly Gly Leu Gly Gly Leu Pro Ser Asn Leu Ser
            100                 105                 110 aca ttg ttc agt caa gcg tac agt gct gga gca agg att cat aca aat     384
Thr Leu Phe Ser Gln Ala Tyr Ser Ala Gly Ala Arg Ile His Thr Asn
        115                 120                 125 tca tgg ggt gct gcg gta aac ggt gct tac acg aca gat tcc aga aac     432
Ser Trp Gly Ala Ala Val Asn Gly Ala Tyr Thr Thr Asp Ser Arg Asn
    130                 135                 140 gta gat gat tat gtt cgt aaa aat gac atg gcg gtt ctt ttt gca gct     480
Val Asp Asp Tyr Val Arg Lys Asn Asp Met Ala Val Leu Phe Ala Ala
145                 150                 155                 160 ggg aat gaa ggt cca ggc agc agt act gtt aat gca cca ggt acc gcg     528
Gly Asn Glu Gly Pro Gly Ser Ser Thr Val Asn Ala Pro Gly Thr Ala
                165                 170                 175 aaa aat gcc att act gta gga gca aca gaa aac tat cgt cca agc ttt     576
Lys Asn Ala Ile Thr Val Gly Ala Thr Glu Asn Tyr Arg Pro Ser Phe
```

```
                  180                 185                 190
ggt tct tac gcg gac aac atc aac cat gtt gca cag ttc tcc tca cgc    624
Gly Ser Tyr Ala Asp Asn Ile Asn His Val Ala Gln Phe Ser Ser Arg
        195                 200                 205 gga cct act cgt gac ggt cgt atc aaa ccg gac gta atg gcg cca gga    672
Gly Pro Thr Arg Asp Gly Arg Ile Lys Pro Asp Val Met Ala Pro Gly
210                 215                 220 aca ttt atc tta tcc gca cgt tct tcc ctt gca ccg gat tct tct ttc    720
Thr Phe Ile Leu Ser Ala Arg Ser Ser Leu Ala Pro Asp Ser Ser Phe
225                 230                 235                 240 tgg gca aac cat gac agc aaa tat gcc tac atg ggc gga act tcc atg    768
Trp Ala Asn His Asp Ser Lys Tyr Ala Tyr Met Gly Gly Thr Ser Met
            245                 250                 255 gca aca cct att gta gct gga aac gta gca caa tta cgt gag cac ttt    816
Ala Thr Pro Ile Val Ala Gly Asn Val Ala Gln Leu Arg Glu His Phe
        260                 265                 270 atc aaa aac aga ggg atc acg cct aaa cca tct tta ttg aag gct gct    864
Ile Lys Asn Arg Gly Ile Thr Pro Lys Pro Ser Leu Leu Lys Ala Ala
    275                 280                 285 ttg att gct ggt gca acg gat gtt ggt ctt ggc ttc ccg aac ggc aac    912
Leu Ile Ala Gly Ala Thr Asp Val Gly Leu Gly Phe Pro Asn Gly Asn
290                 295                 300 caa ggt tgg ggc cga gta aca ttg gat aag tct tta aat aca gcc ttt    960
Gln Gly Trp Gly Arg Val Thr Leu Asp Lys Ser Leu Asn Thr Ala Phe
305                 310                 315                 320 gtg aat gag aca agc tcc ttg tct aca agc caa aag gca acc tac tcc    1008
Val Asn Glu Thr Ser Ser Leu Ser Thr Ser Gln Lys Ala Thr Tyr Ser
            325                 330                 335 ttc aca gca act gca ggt aag cca ctt aag atc tct cta gta tgg tct    1056
Phe Thr Ala Thr Ala Gly Lys Pro Leu Lys Ile Ser Leu Val Trp Ser
        340                 345                 350 gat gct cct gca agc aca tct gct tct ata aca ctg gta aat gac ctt    1104
Asp Ala Pro Ala Ser Thr Ser Ala Ser Ile Thr Leu Val Asn Asp Leu
    355                 360                 365 gac ttg gtg att act gca cca aac gga acg caa tat gta ggg aac gac    1152
Asp Leu Val Ile Thr Ala Pro Asn Gly Thr Gln Tyr Val Gly Asn Asp
370                 375                 380 ttc acg gct cct tat aac aat aat tgg gac gga cgt aat aac gtg gag    1200
Phe Thr Ala Pro Tyr Asn Asn Asn Trp Asp Gly Arg Asn Asn Val Glu
385                 390                 395                 400 aat gta ttc gtc aat gct cca caa agt ggg aca tat acg ata gag gtt    1248
Asn Val Phe Val Asn Ala Pro Gln Ser Gly Thr Tyr Thr Ile Glu Val
            405                 410                 415 caa gca tac aat gta cct caa gga cca cag gcg ttt tca ttg gcg att    1296
Gln Ala Tyr Asn Val Pro Gln Gly Pro Gln Ala Phe Ser Leu Ala Ile
        420                 425                 430 gtg aac taa                                                        1305
Val Asn

<210> SEQ ID NO 2
<211> LENGTH: 434
<212> TYPE: PRT
<213> ORGANISM: Artificial sequence
<220> FEATURE:
<223> OTHER INFORMATION: Synthetic Construct

<400> SEQUENCE: 2

Asn Asp Val Ala Arg Gly Ile Val Lys Ala Asp Val Ala Gln Ser Ser
1               5                   10                  15

Tyr Gly Leu Tyr Gly Gln Gly Gln Thr Val Ala Val Ala Asp Thr Gly
            20                  25                  30
```

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ser Asn Asp
 50                  55                  60

Pro Asn Gly His Gly Thr His Val Ala Gly Val Leu Gly Asn Gly
 65                  70                  75                  80

Thr Ser Asn Lys Gly Met Ala Pro Gln Ala Asn Leu Val Phe Gln Ser
                 85                  90                  95

Ile Met Asp Ser Gly Gly Leu Gly Leu Pro Ser Asn Leu Ser
                100                 105                 110

Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
        130                 135                 140

Val Asp Asp Tyr Val Arg Lys Asn Asp Met Ala Val Leu Phe Ala Ala
145                 150                 155                 160

Gly Asn Glu Gly Pro Gly Ser Ser Thr Val Asn Ala Pro Gly Thr Ala
                    165                 170                 175

Lys Asn Ala Ile Thr Val Gly Ala Thr Glu Asn Tyr Arg Pro Ser Phe
                180                 185                 190

Gly Ser Tyr Ala Asp Asn Ile Asn His Val Ala Gln Phe Ser Ser Arg
            195                 200                 205

Gly Pro Thr Arg Asp Gly Arg Ile Lys Pro Asp Val Met Ala Pro Gly
        210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                    245                 250                 255

Ala Thr Pro Ile Val Ala Gly Asn Val Ala Gln Leu Arg Glu His Phe
                260                 265                 270

Ile Lys Asn Arg Gly Ile Thr Pro Lys Pro Ser Leu Leu Lys Ala Ala
            275                 280                 285

Leu Ile Ala Gly Ala Thr Asp Val Gly Leu Gly Phe Pro Asn Gly Asn
        290                 295                 300

Gln Gly Trp Gly Arg Val Thr Leu Asp Lys Ser Leu Asn Thr Ala Phe
305                 310                 315                 320

Val Asn Glu Thr Ser Ser Leu Ser Thr Ser Gln Lys Ala Thr Tyr Ser
                    325                 330                 335

Phe Thr Ala Thr Ala Gly Lys Pro Leu Lys Ile Ser Leu Val Trp Ser
                340                 345                 350

Asp Ala Pro Ala Ser Thr Ser Ala Ser Ile Thr Leu Val Asn Asp Leu
            355                 360                 365

Asp Leu Val Ile Thr Ala Pro Asn Gly Thr Gln Tyr Val Gly Asn Asp
        370                 375                 380

Phe Thr Ala Pro Tyr Asn Asn Asn Trp Asp Gly Arg Asn Asn Val Glu
385                 390                 395                 400

Asn Val Phe Val Asn Ala Pro Gln Ser Gly Thr Tyr Thr Ile Glu Val
                    405                 410                 415

Gln Ala Tyr Asn Val Pro Gln Gly Pro Gln Ala Phe Ser Leu Ala Ile
                420                 425                 430

Val Asn

<210> SEQ ID NO 3

```
<211> LENGTH: 1305
<212> TYPE: DNA
<213> ORGANISM: Artificial sequence
<220> FEATURE:
<223> OTHER INFORMATION: Strain PD456
<220> FEATURE:
<221> NAME/KEY: CDS
<222> LOCATION: (1)..(1305)

<400> SEQUENCE: 3 aat gat gta gca aga ggc att gtt aaa gcg gat gtc gct caa agc agc        48
Asn Asp Val Ala Arg Gly Ile Val Lys Ala Asp Val Ala Gln Ser Ser
1               5                   10                  15 tac gga ttg tac gga caa gga caa gtt gtt gct gtg gca gac aca ggg        96
Tyr Gly Leu Tyr Gly Gln Gly Gln Val Val Ala Val Ala Asp Thr Gly
            20                  25                  30 ctt gat acc ggc gcc aac gac acc tcc atg cat gaa gct ttc cgc ggg       144
Leu Asp Thr Gly Arg Asn Asp Thr Ser Met His Glu Ala Phe Arg Gly
        35                  40                  45 aaa att act gct tta tat gca tta gga aga tcc aat aac tcc aat gat       192
Lys Ile Thr Ala Leu Tyr Ala Leu Gly Arg Ser Asn Asn Ser Asn Asp
    50                  55                  60 cca aat ggg cat ggt acg cac gtt gcc ggg tct gta ctt gga aac gga       240
Pro Asn Gly His Gly Thr His Val Ala Gly Ser Val Leu Gly Asn Gly
65                  70                  75                  80 gca acc aat aaa ggg atg gca cca cag gca aac ctt gta ttc caa tct       288
Ala Thr Asn Lys Gly Met Ala Pro Gln Ala Asn Leu Val Phe Gln Ser
                85                  90                  95 atc atg gac agc agc ggc gga tta ggg gga ctt cca tcg aat ctc agt       336
Ile Met Asp Ser Ser Gly Gly Leu Gly Gly Leu Pro Ser Asn Leu Ser
            100                 105                 110 aca ttg ttc agc caa gcc tac tct gct ggg gca cgc att cac acc aac       384
Thr Leu Phe Ser Gln Ala Tyr Ser Ala Gly Ala Arg Ile His Thr Asn
        115                 120                 125 tcc tgg gga gct gca gtg aat gga gcg tat acg act gat tcc aga aac       432
Ser Trp Gly Ala Ala Val Asn Gly Ala Tyr Thr Thr Asp Ser Arg Asn
    130                 135                 140 gtg gat gat tat gtt cgt aaa aat gac atg gcc gtt ctt ttc gca gca       480
Val Asp Asp Tyr Val Arg Lys Asn Asp Met Ala Val Leu Phe Ala Ala
145                 150                 155                 160 ggg aat gaa gga cct aac ggt gga acc atc agt gca ccg ggt act gcg       528
Gly Asn Glu Gly Pro Asn Gly Gly Thr Ile Ser Ala Pro Gly Thr Ala
                165                 170                 175 aaa aac gcg atc aca gtc gga gca act gaa aat cta cgt cca agc ttc       576
Lys Asn Ala Ile Thr Val Gly Ala Thr Glu Asn Leu Arg Pro Ser Phe
            180                 185                 190 gga tct tat gca gac aac atc aac cat gtt gca cag ttc tct tcc cgt       624
Gly Ser Tyr Ala Asp Asn Ile Asn His Val Ala Gln Phe Ser Ser Arg
        195                 200                 205 gga cct act cgt gac ggc cgt atc aag ccg gac gta atg gca cct gga       672
Gly Pro Thr Arg Asp Gly Arg Ile Lys Pro Asp Val Met Ala Pro Gly
    210                 215                 220 aca ttt att cta tcg gca cgc tct tcc ctt gca ccg gat tct tct ttc       720
Thr Phe Ile Leu Ser Ala Arg Ser Ser Leu Ala Pro Asp Ser Ser Phe
225                 230                 235                 240 tgg gca aac cat gac agc aaa tat gcc tac atg ggt gga act tcc atg       768
Trp Ala Asn His Asp Ser Lys Tyr Ala Tyr Met Gly Gly Thr Ser Met
                245                 250                 255 gca aca ccg att gtt gct ggg aac gtg gca caa tta cgt gag cac ttt       816
Ala Thr Pro Ile Val Ala Gly Asn Val Ala Gln Leu Arg Glu His Phe
            260                 265                 270 atc aaa aac aga ggc atc aca cct aaa cca tct tta ttg aag gct gca       864
Ile Lys Asn Arg Gly Ile Thr Pro Lys Pro Ser Leu Leu Lys Ala Ala
```

```
                                                                -continued

Ile Lys Asn Arg Gly Ile Thr Pro Lys Pro Ser Leu Leu Lys Ala Ala
        275                 280                 285 cta atc gct ggt gcg acg gat gtt gga tta gga ttc ccg aac gga aac    912
Leu Ile Ala Gly Ala Thr Asp Val Gly Leu Gly Phe Pro Asn Gly Asn
    290                 295                 300 caa ggt tgg ggc cgt gta aca atg gac aag tct tta aat aca aca ttt    960
Gln Gly Trp Gly Arg Val Thr Met Asp Lys Ser Leu Asn Thr Thr Phe
305                 310                 315                 320 gtg aac gag aca aca tcc ctt tct aca agc caa aaa gca acc tat tct   1008
Val Asn Glu Thr Thr Ser Leu Ser Thr Ser Gln Lys Ala Thr Tyr Ser
                325                 330                 335 atc act gca act gca ggc aag cca ctt aag atc tct cta gta tgg tct   1056
Ile Thr Ala Thr Ala Gly Lys Pro Leu Lys Ile Ser Leu Val Trp Ser
            340                 345                 350 gat gct cct gcc agc aca tcc gct tct gtg acg ctg gta aat gac ctt   1104
Asp Ala Pro Ala Ser Thr Ser Ala Ser Val Thr Leu Val Asn Asp Leu
        355                 360                 365 gac ttg gta atc acg gct ccg aac gga acg caa tat gta gga aac gac   1152
Asp Leu Val Ile Thr Ala Pro Asn Gly Thr Gln Tyr Val Gly Asn Asp
    370                 375                 380 ttt acc gct cca ttt aac aat aac tgg gac ggc cgt aat aac gtg gag   1200
Phe Thr Ala Pro Phe Asn Asn Asn Trp Asp Gly Arg Asn Asn Val Glu
385                 390                 395                 400 aat gta ttt atc aat gct ccg cag agt gga acg tat aca gta gag gtt   1248
Asn Val Phe Ile Asn Ala Pro Gln Ser Gly Thr Tyr Thr Val Glu Val
                405                 410                 415 cag gca tac aat gta cct caa gga cca cag gcg ttt tca ttg gcg att   1296
Gln Ala Tyr Asn Val Pro Gln Gly Pro Gln Ala Phe Ser Leu Ala Ile
            420                 425                 430 gtg aac taa                                                       1305
Val Asn

<210> SEQ ID NO 4
<211> LENGTH: 434
<212> TYPE: PRT
<213> ORGANISM: Artificial sequence
<220> FEATURE:
<223> OTHER INFORMATION: Synthetic Construct

<400> SEQUENCE: 4

Asn Asp Val Ala Arg Gly Ile Val Lys Ala Asp Val Ala Gln Ser Ser
1               5                   10                  15

Tyr Gly Leu Tyr Gly Gln Gly Gln Val Val Ala Val Ala Asp Thr Gly
            20                  25                  30

Leu Asp Thr Gly Arg Asn Asp Thr Ser Met His Glu Ala Phe Arg Gly
        35                  40                  45

Lys Ile Thr Ala Leu Tyr Ala Leu Gly Arg Ser Asn Asn Ser Asn Asp
    50                  55                  60

Pro Asn Gly His Gly Thr His Val Ala Gly Ser Val Leu Gly Asn Gly
65                  70                  75                  80

Ala Thr Asn Lys Gly Met Ala Pro Gln Ala Asn Leu Val Phe Gln Ser
                85                  90                  95

Ile Met Asp Ser Ser Gly Gly Leu Gly Leu Pro Ser Asn Leu Ser
                100                 105                 110

Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
        130                 135                 140

Val Asp Asp Tyr Val Arg Lys Asn Asp Met Ala Val Leu Phe Ala Ala
```

-continued

```
                145                 150                 155                 160
Gly Asn Glu Gly Pro Asn Gly Gly Thr Ile Ser Ala Pro Gly Thr Ala
                    165                 170                 175
Lys Asn Ala Ile Thr Val Gly Ala Thr Glu Asn Leu Arg Pro Ser Phe
                180                 185                 190
Gly Ser Tyr Ala Asp Asn Ile Asn His Val Ala Gln Phe Ser Ser Arg
            195                 200                 205
Gly Pro Thr Arg Asp Gly Arg Ile Lys Pro Asp Val Met Ala Pro Gly
        210                 215                 220
Thr Phe Ile Leu Ser Ala Arg Ser Ser Leu Ala Pro Asp Ser Ser Phe
225                 230                 235                 240
Trp Ala Asn His Asp Ser Lys Tyr Ala Tyr Met Gly Gly Thr Ser Met
                245                 250                 255
Ala Thr Pro Ile Val Ala Gly Asn Val Ala Gln Leu Arg Glu His Phe
                260                 265                 270
Ile Lys Asn Arg Gly Ile Thr Pro Lys Pro Ser Leu Leu Lys Ala Ala
            275                 280                 285
Leu Ile Ala Gly Ala Thr Asp Val Gly Leu Gly Phe Pro Asn Gly Asn
        290                 295                 300
Gln Gly Trp Gly Arg Val Thr Met Asp Lys Ser Leu Asn Thr Thr Phe
305                 310                 315                 320
Val Asn Glu Thr Thr Ser Leu Ser Thr Ser Gln Lys Ala Thr Tyr Ser
                325                 330                 335
Ile Thr Ala Thr Ala Gly Lys Pro Leu Lys Ile Ser Leu Val Trp Ser
                340                 345                 350
Asp Ala Pro Ala Ser Thr Ser Ala Ser Val Thr Leu Val Asn Asp Leu
            355                 360                 365
Asp Leu Val Ile Thr Ala Pro Asn Gly Thr Gln Tyr Val Gly Asn Asp
        370                 375                 380
Phe Thr Ala Pro Phe Asn Asn Asn Trp Asp Gly Arg Asn Asn Val Glu
385                 390                 395                 400
Asn Val Phe Ile Asn Ala Pro Gln Ser Gly Thr Tyr Thr Val Glu Val
                405                 410                 415
Gln Ala Tyr Asn Val Pro Gln Gly Pro Gln Ala Phe Ser Leu Ala Ile
                420                 425                 430
Val Asn

<210> SEQ ID NO 5
<211> LENGTH: 1305
<212> TYPE: DNA
<213> ORGANISM: Artificial sequence
<220> FEATURE:
<223> OTHER INFORMATION: JP170/JP40 hybrid
<220> FEATURE:
<221> NAME/KEY: CDS
<222> LOCATION: (1)..(1305)

<400> SEQUENCE: 5 aat gac gtg gcc cgt ggc att gtg aaa gca gac gtc gca caa aat aac    48
Asn Asp Val Ala Arg Gly Ile Val Lys Ala Asp Val Ala Gln Asn Asn
1               5                   10                  15 ttt gga tta tat gga caa gga cag att gta gca gtt gct gat act ggg    96
Phe Gly Leu Tyr Gly Gln Gly Gln Ile Val Ala Val Ala Asp Thr Gly
            20                  25                  30 ctt gat aca gga aga aat gac agt tcg atg cat gaa gca ttc cgc gga   144
Leu Asp Thr Gly Arg Asn Asp Ser Ser Met His Glu Ala Phe Arg Gly
        35                  40                  45
```

```
aaa att acc gcg tta tat gca tta gga aga tcc aat aat tcc aac gac      192
Lys Ile Thr Ala Leu Tyr Ala Leu Gly Arg Ser Asn Asn Ser Asn Asp
 50              55                  60 ccg aac ggt cat ggt aca cac gtt gcc gga tct gta ctt gga aac ggg      240
Pro Asn Gly His Gly Thr His Val Ala Gly Ser Val Leu Gly Asn Gly
 65              70                  75                  80 gca acc aat aaa gga atg gca ccg cag gca aac ctt gtg ttc caa tcc      288
Ala Thr Asn Lys Gly Met Ala Pro Gln Ala Asn Leu Val Phe Gln Ser
                 85                  90                  95 atc atg gat agc agc ggc gga ttg gga ggc ctt cca tcc aac ctg agc      336
Ile Met Asp Ser Ser Gly Gly Leu Gly Gly Leu Pro Ser Asn Leu Ser
            100                 105                 110 aca cta ttc agc caa gct tac agc gcc gga gca aga att cat acg aac      384
Thr Leu Phe Ser Gln Ala Tyr Ser Ala Gly Ala Arg Ile His Thr Asn
        115                 120                 125 tca tgg ggt gct gcg gta aac ggc gct tac acg aca gat tcc aga aat      432
Ser Trp Gly Ala Ala Val Asn Gly Ala Tyr Thr Thr Asp Ser Arg Asn
130                 135                 140 gtc gat gac tat gtt cgt aaa aat gac atg gct gtt ctt ttc gca gcc      480
Val Asp Asp Tyr Val Arg Lys Asn Asp Met Ala Val Leu Phe Ala Ala
145                 150                 155                 160 ggg aat gaa ggg ccg aac agt ggc acc atc agt gca cct ggt aca gcg      528
Gly Asn Glu Gly Pro Asn Ser Gly Thr Ile Ser Ala Pro Gly Thr Ala
                165                 170                 175 aaa aat gcc att aca gtt gga gct aca gaa aac tat cgt cca agc ttt      576
Lys Asn Ala Ile Thr Val Gly Ala Thr Glu Asn Tyr Arg Pro Ser Phe
            180                 185                 190 gga tct tat gca gac aat atc aat cat gtt gca caa ttc tcc tct cgc      624
Gly Ser Tyr Ala Asp Asn Ile Asn His Val Ala Gln Phe Ser Ser Arg
        195                 200                 205 gga cct act cgt gac ggc cga atc aag ccg gat gta atg gcg cca gga      672
Gly Pro Thr Arg Asp Gly Arg Ile Lys Pro Asp Val Met Ala Pro Gly
210                 215                 220 aca ttt att tta tca gca cgc tct tcc ctt gcg ccg gat tct tcc ttc      720
Thr Phe Ile Leu Ser Ala Arg Ser Ser Leu Ala Pro Asp Ser Ser Phe
225                 230                 235                 240 tgg gca aac cat gac agc aaa tat gct tac atg ggt gga act tcc atg      768
Trp Ala Asn His Asp Ser Lys Tyr Ala Tyr Met Gly Gly Thr Ser Met
                245                 250                 255 gca aca ccg att gtt gca ggg aac gtg gca caa tta cgt gag cac ttt      816
Ala Thr Pro Ile Val Ala Gly Asn Val Ala Gln Leu Arg Glu His Phe
            260                 265                 270 atc aaa aac aga ggc atc aca cct aaa ccg tcc tta ttg aag gct gcg      864
Ile Lys Asn Arg Gly Ile Thr Pro Lys Pro Ser Leu Leu Lys Ala Ala
        275                 280                 285 cta att gcg ggt gcc act gat gtt ggt ctt gga ttc cct aac ggc aac      912
Leu Ile Ala Gly Ala Thr Asp Val Gly Leu Gly Phe Pro Asn Gly Asn
290                 295                 300 caa ggt tgg ggc cgt gtg aca ttg gat aag tct tta aac act gca ttt      960
Gln Gly Trp Gly Arg Val Thr Leu Asp Lys Ser Leu Asn Thr Ala Phe
305                 310                 315                 320 gtg aat gag aca agc tcc ctg tcc aca agc caa aag gca acg tac tcc     1008
Val Asn Glu Thr Ser Ser Leu Ser Thr Ser Gln Lys Ala Thr Tyr Ser
                325                 330                 335 ttc aat gca aca tca ggc aag cca ctt aag att tct cta gta tgg tct     1056
Phe Asn Ala Thr Ser Gly Lys Pro Leu Lys Ile Ser Leu Val Trp Ser
            340                 345                 350 gat gct cct gca agc aca tcc gct tct gtg acg tta gta aat gac ctt     1104
Asp Ala Pro Ala Ser Thr Ser Ala Ser Val Thr Leu Val Asn Asp Leu
        355                 360                 365
```

```
gac ttg gtg att act gct ccg aac gga acg aaa tat gtt gga aac gac    1152
Asp Leu Val Ile Thr Ala Pro Asn Gly Thr Lys Tyr Val Gly Asn Asp
    370                 375                 380 ttt act gca cca ttt gat aac aac tgg gat ggc aga aac aac gtg gaa    1200
Phe Thr Ala Pro Phe Asp Asn Asn Trp Asp Gly Arg Asn Asn Val Glu
385                 390                 395                 400 aat gtg ttt atc aat gct cct caa agc gga acg tat aca gtc gaa gtg    1248
Asn Val Phe Ile Asn Ala Pro Gln Ser Gly Thr Tyr Thr Val Glu Val
                405                 410                 415 cag gct tac aat gta cca gta ggt ccg caa acc ttt tct tta gcg att    1296
Gln Ala Tyr Asn Val Pro Val Gly Pro Gln Thr Phe Ser Leu Ala Ile
            420                 425                 430 gta cat taa                                                        1305
Val His

<210> SEQ ID NO 6
<211> LENGTH: 434
<212> TYPE: PRT
<213> ORGANISM: Artificial sequence
<220> FEATURE:
<223> OTHER INFORMATION: Synthetic Construct

<400> SEQUENCE: 6

Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Ser Asn Asn Ser Asn Asp
    50                  55                  60

Pro Asn Gly His Gly Thr His Val Ala Gly Ser Val Leu Gly Asn Gly
65                  70                  75                  80

Ala Thr Asn Lys Gly Met Ala Pro Gln Ala Asn Leu Val Phe Gln Ser
                85                  90                  95

Ile Met Asp Ser Ser Gly Gly Leu Gly Gly Leu Pro Ser Asn Leu Ser
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Ala Val Leu Phe Ala Ala
145                 150                 155                 160

Gly Asn Glu Gly Pro Asn Ser Gly Thr Ile Ser Ala Pro Gly Thr Ala
                165                 170                 175

Lys Asn Ala Ile Thr Val Gly Ala Thr Glu Asn Tyr Arg Pro Ser Phe
            180                 185                 190

Gly Ser Tyr Ala Asp Asn Ile Asn His Val Ala Gln Phe Ser Ser Arg
        195                 200                 205

Gly Pro Thr Arg Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270
```

-continued

```
Ile Lys Asn Arg Gly Ile Thr Pro Lys Pro Ser Leu Leu Lys Ala Ala
    275                 280                 285
Leu Ile Ala Gly Ala Thr Asp Val Gly Leu Gly Phe Pro Asn Gly Asn
290                 295                 300
Gln Gly Trp Gly Arg Val Thr Leu Asp Lys Ser Leu Asn Thr Ala Phe
305                 310                 315                 320
Val Asn Glu Thr Ser Ser Leu Ser Thr Ser Gln Lys Ala Thr Tyr Ser
                325                 330                 335
Phe Asn Ala Thr Ser Gly Lys Pro Leu Lys Ile Ser Leu Val Trp Ser
                340                 345                 350
Asp Ala Pro Ala Ser Thr Ser Ala Ser Val Thr Leu Val Asn Asp Leu
            355                 360                 365
Asp Leu Val Ile Thr Ala Pro Asn Gly Thr Lys Tyr Val Gly Asn Asp
370                 375                 380
Phe Thr Ala Pro Phe Asp Asn Asn Trp Asp Gly Arg Asn Asn Val Glu
385                 390                 395                 400
Asn Val Phe Ile Asn Ala Pro Gln Ser Gly Thr Tyr Thr Val Glu Val
                405                 410                 415
Gln Ala Tyr Asn Val Pro Val Gly Pro Gln Thr Phe Ser Leu Ala Ile
                420                 425                 430
Val His
```

<210> SEQ ID NO 7
<211> LENGTH: 1305
<212> TYPE: DNA
<213> ORGANISM: Artificial sequence
<220> FEATURE:
<223> OTHER INFORMATION: JP170/PD456 hybrid
<220> FEATURE:
<221> NAME/KEY: CDS
<222> LOCATION: (1)..(1305)

<400> SEQUENCE: 7

```
aat gac gtg gcc cgt ggc att gtg aaa gca gac gtc gca caa aat aac      48
Asn Asp Val Ala Arg Gly Ile Val Lys Ala Asp Val Ala Gln Asn Asn
1               5                   10                  15 ttt ggc tta tat gga caa gga cag att gta gca gtt gct gat act ggg      96
Phe Gly Leu Tyr Gly Gln Gly Gln Ile Val Ala Val Ala Asp Thr Gly
            20                  25                  30 ctt gat aca gga aga aat gac agt tcg atg cat gaa gca ttc cgc ggg     144
Leu Asp Thr Gly Arg Asn Asp Ser Ser Met His Glu Ala Phe Arg Gly
        35                  40                  45 aaa att act gct tta tat gca tta gga aga tcc aat aac tcc aat gat     192
Lys Ile Thr Ala Leu Tyr Ala Leu Gly Arg Ser Asn Asn Ser Asn Asp
    50                  55                  60 cca aat ggg cat ggt acg cac gtt gcc ggg tct gta ctt gga aac gga     240
Pro Asn Gly His Gly Thr His Val Ala Gly Ser Val Leu Gly Asn Gly
65                  70                  75                  80 gca acc aat aaa ggg atg gca cca cag gca aac ctt gta ttc caa tct     288
Ala Thr Asn Lys Gly Met Ala Pro Gln Ala Asn Leu Val Phe Gln Ser
                85                  90                  95 atc atg gac agc agc ggc gga tta ggg gga ctt cca tcg aat ctc agt     336
Ile Met Asp Ser Ser Gly Gly Leu Gly Gly Leu Pro Ser Asn Leu Ser
            100                 105                 110 aca ttg ttc agc caa gcc tac tct gct ggg gca cgc att cac acc aac     384
Thr Leu Phe Ser Gln Ala Tyr Ser Ala Gly Ala Arg Ile His Thr Asn
        115                 120                 125 tcc tgg gga gct gca gtg aat gga gcg tat acg act gat tcc aga aac     432
Ser Trp Gly Ala Ala Val Asn Gly Ala Tyr Thr Thr Asp Ser Arg Asn
    130                 135                 140
```

| | | | | | | | | | | | | | | | | |
|---|---|---|---|---|---|---|---|---|---|---|---|---|---|---|---|---|
| gtg | gat | gat | tat | gtt | cgt | aaa | aat | gac | atg | gcc | gtt | ctt | ttc | gca | gca | 480 |
| Val | Asp | Asp | Tyr | Val | Arg | Lys | Asn | Asp | Met | Ala | Val | Leu | Phe | Ala | Ala | |
| 145 | | | | 150 | | | | | 155 | | | | | 160 | | |
| ggg | aat | gaa | gga | cct | aac | ggt | gga | acc | atc | agt | gca | ccg | ggt | act | gcg | 528 |
| Gly | Asn | Glu | Gly | Pro | Asn | Gly | Gly | Thr | Ile | Ser | Ala | Pro | Gly | Thr | Ala | |
| | | | | 165 | | | | | 170 | | | | | 175 | | |
| aaa | aac | gcg | atc | aca | gtc | gga | gca | act | gaa | aat | cta | cgt | cca | agc | ttc | 576 |
| Lys | Asn | Ala | Ile | Thr | Val | Gly | Ala | Thr | Glu | Asn | Leu | Arg | Pro | Ser | Phe | |
| | | | 180 | | | | | 185 | | | | | 190 | | | |
| gga | tct | tat | gca | gac | aac | atc | aac | cat | gtt | gca | cag | ttc | tct | tcc | cgt | 624 |
| Gly | Ser | Tyr | Ala | Asp | Asn | Ile | Asn | His | Val | Ala | Gln | Phe | Ser | Ser | Arg | |
| | | 195 | | | | | 200 | | | | | 205 | | | | |
| gga | cct | act | cgt | gac | ggc | cgt | atc | aag | ccg | gac | gta | atg | gca | cct | gga | 672 |
| Gly | Pro | Thr | Arg | Asp | Gly | Arg | Ile | Lys | Pro | Asp | Val | Met | Ala | Pro | Gly | |
| | 210 | | | | | 215 | | | | | 220 | | | | | |
| aca | ttt | att | cta | tcg | gca | cgc | tct | tcc | ctt | gca | ccg | gat | tct | tct | ttc | 720 |
| Thr | Phe | Ile | Leu | Ser | Ala | Arg | Ser | Ser | Leu | Ala | Pro | Asp | Ser | Ser | Phe | |
| 225 | | | | | 230 | | | | | 235 | | | | | 240 | |
| tgg | gca | aac | cat | gac | agc | aaa | tat | gcc | tac | atg | ggt | gga | act | tcc | atg | 768 |
| Trp | Ala | Asn | His | Asp | Ser | Lys | Tyr | Ala | Tyr | Met | Gly | Gly | Thr | Ser | Met | |
| | | | 245 | | | | | 250 | | | | | 255 | | | |
| gca | aca | ccg | att | att | gct | ggg | aac | gtg | gca | caa | tta | cgt | gag | cac | ttt | 816 |
| Ala | Thr | Pro | Ile | Ile | Ala | Gly | Asn | Val | Ala | Gln | Leu | Arg | Glu | His | Phe | |
| | | 260 | | | | | 265 | | | | | 270 | | | | |
| atc | aaa | aac | aga | ggc | atc | aca | cct | aaa | cca | tct | tta | ttg | aag | gct | gca | 864 |
| Ile | Lys | Asn | Arg | Gly | Ile | Thr | Pro | Lys | Pro | Ser | Leu | Leu | Lys | Ala | Ala | |
| | 275 | | | | | 280 | | | | | 285 | | | | | |
| cta | atc | gct | ggt | gcg | acg | gat | gtt | gga | tta | gga | ttc | ccg | aac | gga | aac | 912 |
| Leu | Ile | Ala | Gly | Ala | Thr | Asp | Val | Gly | Leu | Gly | Phe | Pro | Asn | Gly | Asn | |
| | 290 | | | | | 295 | | | | | 300 | | | | | |
| caa | ggt | tgg | ggc | cgt | gta | aca | atg | gac | aag | tct | tta | aat | aca | aca | ttt | 960 |
| Gln | Gly | Trp | Gly | Arg | Val | Thr | Met | Asp | Lys | Ser | Leu | Asn | Thr | Thr | Phe | |
| 305 | | | | 310 | | | | | 315 | | | | | 320 | | |
| gtg | aac | gag | aca | aca | tcc | ctt | tct | aca | agc | caa | aaa | gca | acc | tat | tct | 1008 |
| Val | Asn | Glu | Thr | Thr | Ser | Leu | Ser | Thr | Ser | Gln | Lys | Ala | Thr | Tyr | Ser | |
| | | | 325 | | | | | 330 | | | | | 335 | | | |
| atc | act | gca | act | gca | ggc | aag | cca | ctt | aag | atc | tct | cta | gta | tgg | tct | 1056 |
| Ile | Thr | Ala | Thr | Ala | Gly | Lys | Pro | Leu | Lys | Ile | Ser | Leu | Val | Trp | Ser | |
| | | | 340 | | | | | 345 | | | | | 350 | | | |
| gat | gct | cct | gcc | agc | aca | tcc | gct | tct | gtg | acg | ctg | gta | aat | gac | ctt | 1104 |
| Asp | Ala | Pro | Ala | Ser | Thr | Ser | Ala | Ser | Val | Thr | Leu | Val | Asn | Asp | Leu | |
| | | 355 | | | | | 360 | | | | | 365 | | | | |
| gac | ttg | gta | atc | acg | gct | ccg | aac | gga | acg | caa | tat | gta | gga | aac | gac | 1152 |
| Asp | Leu | Val | Ile | Thr | Ala | Pro | Asn | Gly | Thr | Gln | Tyr | Val | Gly | Asn | Asp | |
| | 370 | | | | | 375 | | | | | 380 | | | | | |
| ttt | acc | gct | cca | ttt | aac | aat | aac | cgg | gat | ggc | aga | aac | aac | gtg | gaa | 1200 |
| Phe | Thr | Ala | Pro | Phe | Asn | Asn | Asn | Arg | Asp | Gly | Arg | Asn | Asn | Val | Glu | |
| 385 | | | | 390 | | | | | 395 | | | | | 400 | | |
| aat | gtg | ttt | atc | aat | gct | cct | caa | agc | gga | acg | tat | aca | gtc | gaa | gtg | 1248 |
| Asn | Val | Phe | Ile | Asn | Ala | Pro | Gln | Ser | Gly | Thr | Tyr | Thr | Val | Glu | Val | |
| | | | | 405 | | | | | 410 | | | | | 415 | | |
| cag | gct | tac | aat | gta | cca | gta | ggt | ccg | caa | acc | ttt | tct | tta | gcg | att | 1296 |
| Gln | Ala | Tyr | Asn | Val | Pro | Val | Gly | Pro | Gln | Thr | Phe | Ser | Leu | Ala | Ile | |
| | | | 420 | | | | | 425 | | | | | 430 | | | |
| gta | cat | taa | | | | | | | | | | | | | | 1305 |
| Val | His | | | | | | | | | | | | | | | |

<210> SEQ ID NO 8
<211> LENGTH: 434
<212> TYPE: PRT

-continued

<213> ORGANISM: Artificial sequence
<220> FEATURE:
<223> OTHER INFORMATION: Synthetic Construct

<400> SEQUENCE: 8

```
Asn Asp Val Ala Arg Gly Ile Val Lys Ala Asp Val Ala Gln Asn Asn
 1               5                  10                  15

Phe Gly Leu Tyr Gly Gln Gly Gln Ile Val Ala Val Ala Asp Thr Gly
                20                  25                  30

Leu Asp Thr Gly Arg Asn Asp Ser Ser Met His Glu Ala Phe Arg Gly
             35                  40                  45

Lys Ile Thr Ala Leu Tyr Ala Leu Gly Arg Ser Asn Asn Ser Asn Asp
 50                  55                  60

Pro Asn Gly His Gly Thr His Val Ala Gly Ser Val Leu Gly Asn Gly
 65                  70                  75                  80

Ala Thr Asn Lys Gly Met Ala Pro Gln Ala Asn Leu Val Phe Gln Ser
                 85                  90                  95

Ile Met Asp Ser Ser Gly Gly Leu Gly Gly Leu Pro Ser Asn Leu Ser
                100                 105                 110

Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
130                 135                 140

Val Asp Asp Tyr Val Arg Lys Asn Asp Met Ala Val Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Arg Asp Gly Arg Ile Lys Pro Asp Val Met Ala Pro Gly
210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Ile Ala Gly Asn Val Ala Gln Leu Arg Glu His Phe
            260                 265                 270

Ile Lys Asn Arg Gly Ile Thr Pro Lys Pro Ser Leu Leu Lys Ala Ala
        275                 280                 285

Leu Ile Ala Gly Ala Thr Asp Val Gly Leu Gly Phe Pro Asn Gly Asn
    290                 295                 300

Gln Gly Trp Gly Arg Val Thr Met Asp Lys Ser Leu Asn Thr Thr Phe
305                 310                 315                 320

Val Asn Glu Thr Thr Ser Leu Ser Thr Ser Gln Lys Ala Thr Tyr Ser
                325                 330                 335

Ile Thr Ala Thr Ala Gly Lys Pro Leu Lys Ile Ser Leu Val Trp Ser
            340                 345                 350

Asp Ala Pro Ala Ser Thr Ser Ala Ser Val Thr Leu Val Asn Asp Leu
        355                 360                 365

Asp Leu Val Ile Thr Ala Pro Asn Gly Thr Gln Tyr Val Gly Asn Asp
    370                 375                 380

Phe Thr Ala Pro Phe Asn Asn Asn Arg Asp Gly Arg Asn Asn Val Glu
385                 390                 395                 400
```

```
Asn Val Phe Ile Asn Ala Pro Gln Ser Gly Thr Tyr Thr Val Glu Val
                405                 410                 415
Gln Ala Tyr Asn Val Pro Val Gly Pro Gln Thr Phe Ser Leu Ala Ile
            420                 425                 430
Val His

<210> SEQ ID NO 9
<211> LENGTH: 1305
<212> TYPE: DNA
<213> ORGANISM: Artificial sequence
<220> FEATURE:
<223> OTHER INFORMATION: JP170/JP75 hybrid
<220> FEATURE:
<221> NAME/KEY: CDS
<222> LOCATION: (1)..(1305)

<400> SEQUENCE: 9 aat gac gtg gcc cgt ggc att gtg aaa gca gac gtc gca caa aat aac      48
Asn Asp Val Ala Arg Gly Ile Val Lys Ala Asp Val Ala Gln Asn Asn
1               5                   10                  15 ttt ggc tta tat gga caa gga cag att gta gca gtt gct gat act ggg      96
Phe Gly Leu Tyr Gly Gln Gly Gln Ile Val Ala Val Ala Asp Thr Gly
            20                  25                  30 ctt gat aca gga aga aat gac agt tcg atg cat gaa gca ttc cgc gga     144
Leu Asp Thr Gly Arg Asn Asp Ser Ser Met His Glu Ala Phe Arg Gly
        35                  40                  45 aaa att aca gct tta tac gca tta gga aga tcc aat aat tcc aac gac     192
Lys Ile Thr Ala Leu Tyr Ala Leu Gly Arg Ser Asn Asn Ser Asn Asp
    50                  55                  60 ccg aac ggt cat ggt aca cac gtt gcc gga tct gta ctt gga aac ggg     240
Pro Asn Gly His Gly Thr His Val Ala Gly Ser Val Leu Gly Asn Gly
65                  70                  75                  80 gca acc aat aaa gga atg gca ccg cag gca aat ctt gta ttc caa tcc     288
Ala Thr Asn Lys Gly Met Ala Pro Gln Ala Asn Leu Val Phe Gln Ser
                85                  90                  95 atc atg gat agc agc ggc gga ttg gga ggc ctt cca tcc aac ctg agc     336
Ile Met Asp Ser Ser Gly Gly Leu Gly Gly Leu Pro Ser Asn Leu Ser
            100                 105                 110 aca ttg ttt agt caa gct tac act gcc ggg gcc cga att cac acc aac     384
Thr Leu Phe Ser Gln Ala Tyr Thr Ala Gly Ala Arg Ile His Thr Asn
        115                 120                 125 tcc tgg ggt gct gcg gta aat ggc gct tac aca aca gat tcc aga aac     432
Ser Trp Gly Ala Ala Val Asn Gly Ala Tyr Thr Thr Asp Ser Arg Asn
    130                 135                 140 gtt gat gac tat gtt cgt aaa aat gat atg gct gtt ctt ttc gca gct     480
Val Asp Asp Tyr Val Arg Lys Asn Asp Met Ala Val Leu Phe Ala Ala
145                 150                 155                 160 ggg aat gaa gga cct aat agt ggc acc atc agt gca ccg ggt act gcg     528
Gly Asn Glu Gly Pro Asn Ser Gly Thr Ile Ser Ala Pro Gly Thr Ala
                165                 170                 175 aaa aat gcc att aca gtt gga gca aca gaa aat tat cgt cca agc ttt     576
Lys Asn Ala Ile Thr Val Gly Ala Thr Glu Asn Tyr Arg Pro Ser Phe
            180                 185                 190 ggg tct tat gca gac aat atc aat cat gtt gca cag ttc tct tca cgc     624
Gly Ser Tyr Ala Asp Asn Ile Asn His Val Ala Gln Phe Ser Ser Arg
        195                 200                 205 gga cct act cgt gac ggt cga atc aag ccg gac gta atg gcg cca gga     672
Gly Pro Thr Arg Asp Gly Arg Ile Lys Pro Asp Val Met Ala Pro Gly
    210                 215                 220 acc ttt att tta tca gca cgc tct tcc ctt gca cca gat tct tcc ttc     720
Thr Phe Ile Leu Ser Ala Arg Ser Ser Leu Ala Pro Asp Ser Ser Phe
```

```
tgg gca aac cat gat agc aaa tat gct tac atg ggc gga act tcc atg    768
Trp Ala Asn His Asp Ser Lys Tyr Ala Tyr Met Gly Gly Thr Ser Met
                245                 250                 255 gca aca ccg att gtt gcc gga aac gtg gca caa tta cgt gag cac ttt    816
Ala Thr Pro Ile Val Ala Gly Asn Val Ala Gln Leu Arg Glu His Phe
            260                 265                 270 atc aaa aac aga ggc atc aca cct aag ccg tcc tta ttg aag gct gct    864
Ile Lys Asn Arg Gly Ile Thr Pro Lys Pro Ser Leu Leu Lys Ala Ala
        275                 280                 285 ctt att gct ggt gcc act gat gtg ggt ctt gga ttc ccg aac ggc aac    912
Leu Ile Ala Gly Ala Thr Asp Val Gly Leu Gly Phe Pro Asn Gly Asn
    290                 295                 300 caa ggt tgg gga cgt gtg aca ttg gat aag tct tta aac acc gcg ttc    960
Gln Gly Trp Gly Arg Val Thr Leu Asp Lys Ser Leu Asn Thr Ala Phe
305                 310                 315                 320 gtg aat gag aca agc tcc ctg tcc aca agc caa aag gcg acg tat tcc   1008
Val Asn Glu Thr Ser Ser Leu Ser Thr Ser Gln Lys Ala Thr Tyr Ser
                325                 330                 335 ttt aat gca aca gca ggc aag cca ctt aag atc tct cta gta tgg tct   1056
Phe Asn Ala Thr Ala Gly Lys Pro Leu Lys Ile Ser Leu Val Trp Ser
            340                 345                 350 gat gct cct gca agc aca tcc gct tct ata aca tta gta aat gac ctt   1104
Asp Ala Pro Ala Ser Thr Ser Ala Ser Ile Thr Leu Val Asn Asp Leu
        355                 360                 365 gac ttg gtg att acc gct cca aac gga acg aaa tat gtt gga aac gac   1152
Asp Leu Val Ile Thr Ala Pro Asn Gly Thr Lys Tyr Val Gly Asn Asp
    370                 375                 380 ttt act gca cca ttt gat aac aac tgg gat ggc aga aac aac gtg gaa   1200
Phe Thr Ala Pro Phe Asp Asn Asn Trp Asp Gly Arg Asn Asn Val Glu
385                 390                 395                 400 aat gtg ttt atc aat gct cct caa agc gga acg tat aca gtc gaa gtg   1248
Asn Val Phe Ile Asn Ala Pro Gln Ser Gly Thr Tyr Thr Val Glu Val
                405                 410                 415 cag gct tac aat gta cca gta ggt ccg caa acc ttt tct tta gcg att   1296
Gln Ala Tyr Asn Val Pro Val Gly Pro Gln Thr Phe Ser Leu Ala Ile
            420                 425                 430 gta cat taa                                                       1305
Val His

<210> SEQ ID NO 10
<211> LENGTH: 434
<212> TYPE: PRT
<213> ORGANISM: Artificial sequence
<220> FEATURE:
<223> OTHER INFORMATION: Synthetic Construct

<400> SEQUENCE: 10

Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Ser Asn Asn Ser Asn Asp
    50                  55                  60

Pro Asn Gly His Gly Thr His Val Ala Gly Ser Val Leu Gly Asn Gly
65                  70                  75                  80

Ala Thr Asn Lys Gly Met Ala Pro Gln Ala Asn Leu Val Phe Gln Ser
                85                  90                  95
```

```
Ile Met Asp Ser Ser Gly Gly Leu Gly Gly Leu Pro Ser Asn Leu Ser
            100                 105                 110

Thr Leu Phe Ser Gln Ala Tyr Thr Ala Gly Ala Arg Ile His Thr Asn
        115                 120                 125

Ser Trp Gly Ala Ala Val Asn Gly Ala Tyr Thr Asp Ser Arg Asn
    130                 135                 140

Val Asp Asp Tyr Val Arg Lys Asn Asp Met Ala Val Leu Phe Ala Ala
145                 150                 155                 160

Gly Asn Glu Gly Pro Asn Ser Gly Thr Ile Ser Ala Pro Gly Thr Ala
                165                 170                 175

Lys Asn Ala Ile Thr Val Gly Ala Thr Glu Asn Tyr Arg Pro Ser Phe
                180                 185                 190

Gly Ser Tyr Ala Asp Asn Ile Asn His Val Ala Gln Phe Ser Ser Arg
                195                 200                 205

Gly Pro Thr Arg Asp Gly Arg Ile Lys Pro Asp Val Met Ala Pro Gly
            210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
            275                 280                 285

Leu Ile Ala Gly Ala Thr Asp Val Gly Leu Gly Phe Pro Asn Gly Asn
            290                 295                 300

Gln Gly Trp Gly Arg Val Thr Leu Asp Lys Ser Leu Asn Thr Ala Phe
305                 310                 315                 320

Val Asn Glu Thr Ser Ser Leu Ser Thr Ser Gln Lys Ala Thr Tyr Ser
                325                 330                 335

Phe Asn Ala Thr Ala Gly Lys Pro Leu Lys Ile Ser Leu Val Trp Ser
            340                 345                 350

Asp Ala Pro Ala Ser Thr Ser Ala Ser Ile Thr Leu Val Asn Asp Leu
            355                 360                 365

Asp Leu Val Ile Thr Ala Pro Asn Gly Thr Lys Tyr Val Gly Asn Asp
        370                 375                 380

Phe Thr Ala Pro Phe Asp Asn Asn Trp Asp Gly Arg Asn Asn Val Glu
385                 390                 395                 400

Asn Val Phe Ile Asn Ala Pro Gln Ser Gly Thr Tyr Thr Val Glu Val
                405                 410                 415

Gln Ala Tyr Asn Val Pro Val Gly Pro Gln Thr Phe Ser Leu Ala Ile
            420                 425                 430

Val His

<210> SEQ ID NO 11
<211> LENGTH: 1305
<212> TYPE: DNA
<213> ORGANISM: Artificial sequence
<220> FEATURE:
<223> OTHER INFORMATION: JP170/JT169 hybrid
<220> FEATURE:
<221> NAME/KEY: CDS
<222> LOCATION: (1)..(1305)

<400> SEQUENCE: 11 aat gac gtg gcc cgt ggc att gtg aaa gca gac gtc gca caa aat aac       48
```

```
Asn Asp Val Ala Arg Gly Ile Val Lys Ala Asp Val Ala Gln Asn Asn
1               5                   10                  15 ttt ggc tta tat gga caa gga cag att gta gca gtt gct gat act ggg      96
Phe Gly Leu Tyr Gly Gln Gly Gln Ile Val Ala Val Ala Asp Thr Gly
                20                  25                  30 ctt gat aca gga aga aat gac agt tcg atg cat gaa gcg ttc cgc gga    144
Leu Asp Thr Gly Arg Asn Asp Ser Ser Met His Glu Ala Phe Arg Gly
            35                  40                  45 aaa atc act gcg ttg tat gcc tta gga aga acc aat aat tcc aac gat    192
Lys Ile Thr Ala Leu Tyr Ala Leu Gly Arg Thr Asn Asn Ser Asn Asp
        50                  55                  60 cca aat ggt cac gga acg cac gtt gcc gga tct gtt ctt gga aac gga    240
Pro Asn Gly His Gly Thr His Val Ala Gly Ser Val Leu Gly Asn Gly
65                  70                  75                  80 aca agc aat aaa gga atg gcg cca caa gca aat cta gta ttt caa tcc    288
Thr Ser Asn Lys Gly Met Ala Pro Gln Ala Asn Leu Val Phe Gln Ser
                85                  90                  95 atc atg gat agc ggc ggt gga ttg ggc ggc ctt cca tcc aac ctg agc    336
Ile Met Asp Ser Gly Gly Gly Leu Gly Gly Leu Pro Ser Asn Leu Ser
            100                 105                 110 aca ttg ttc agt caa gcg tac agt gct gga gca agg att cat aca aat    384
Thr Leu Phe Ser Gln Ala Tyr Ser Ala Gly Ala Arg Ile His Thr Asn
        115                 120                 125 tca tgg ggt gct gcg gta aac ggt gct tac acg aca gat tcc aga aac    432
Ser Trp Gly Ala Ala Val Asn Gly Ala Tyr Thr Thr Asp Ser Arg Asn
    130                 135                 140 gta gat gat tat gtt cgt aaa aat gac atg gcg gtt ctt ttt gca gct    480
Val Asp Asp Tyr Val Arg Lys Asn Asp Met Ala Val Leu Phe Ala Ala
145                 150                 155                 160 ggg aat gaa ggt cca ggc agc agt act gtt aat gca cca ggt acc gcg    528
Gly Asn Glu Gly Pro Gly Ser Ser Thr Val Asn Ala Pro Gly Thr Ala
                165                 170                 175 aaa aat gcc att act gta gga gca aca gaa aac tat cgt cca agc ttt    576
Lys Asn Ala Ile Thr Val Gly Ala Thr Glu Asn Tyr Arg Pro Ser Phe
            180                 185                 190 ggt tct tac gcg gac aac atc aac cat gtt gca cag ttc tcc tca cgc    624
Gly Ser Tyr Ala Asp Asn Ile Asn His Val Ala Gln Phe Ser Ser Arg
        195                 200                 205 gga cct act cgt gac ggt cgt atc aaa ccg gac gta atg gcg cca gga    672
Gly Pro Thr Arg Asp Gly Arg Ile Lys Pro Asp Val Met Ala Pro Gly
    210                 215                 220 aca ttt atc tta tcc gca cgt tct tcc ctt gca ccg gat tct tct ttc    720
Thr Phe Ile Leu Ser Ala Arg Ser Ser Leu Ala Pro Asp Ser Ser Phe
225                 230                 235                 240 tgg gca aac cat gac agc aaa tat gcc tac atg ggc gga act tcc atg    768
Trp Ala Asn His Asp Ser Lys Tyr Ala Tyr Met Gly Gly Thr Ser Met
                245                 250                 255 gca aca cct att gta gct gga aac gta gca caa tta cgt gag cac ttt    816
Ala Thr Pro Ile Val Ala Gly Asn Val Ala Gln Leu Arg Glu His Phe
            260                 265                 270 atc aaa aac aga ggg atc acg cct aaa cca tct tta ttg aag gct gct    864
Ile Lys Asn Arg Gly Ile Thr Pro Lys Pro Ser Leu Leu Lys Ala Ala
        275                 280                 285 ttg att gct ggt gca acg gat gtt ggt ctt ggc ttc ccg aac ggc aac    912
Leu Ile Ala Gly Ala Thr Asp Val Gly Leu Gly Phe Pro Asn Gly Asn
    290                 295                 300 caa ggt tgg ggc cga gta aca ttg gat aag tct tta aat aca gcc ttt    960
Gln Gly Trp Gly Arg Val Thr Leu Asp Lys Ser Leu Asn Thr Ala Phe
305                 310                 315                 320 gtg aat gag aca agc tcc ttg tct aca agc caa aag gca acc tac tcc   1008
```

```
Val Asn Glu Thr Ser Ser Leu Ser Thr Ser Gln Lys Ala Thr Tyr Ser
            325                 330                 335 ttc aca gca act gca ggt aag cca ctt aag atc tct cta gta tgg tct    1056
Phe Thr Ala Thr Ala Gly Lys Pro Leu Lys Ile Ser Leu Val Trp Ser
            340                 345                 350 gat gct cct gca agc aca tct gct tct ata aca ctg gta aat gac ctt    1104
Asp Ala Pro Ala Ser Thr Ser Ala Ser Ile Thr Leu Val Asn Asp Leu
            355                 360                 365 gac ttg gtg att act gca cca aac gga acg caa tat gta ggg aac gac    1152
Asp Leu Val Ile Thr Ala Pro Asn Gly Thr Gln Tyr Val Gly Asn Asp
    370                 375                 380 ttc acg gct cct tat aac aat aat tgg gat ggc aga aac aac gtg gaa    1200
Phe Thr Ala Pro Tyr Asn Asn Asn Trp Asp Gly Arg Asn Asn Val Glu
385                 390                 395                 400 aat gtg ttt atc aat gct cct caa agc gga acg tat aca gtc gaa gtg    1248
Asn Val Phe Ile Asn Ala Pro Gln Ser Gly Thr Tyr Thr Val Glu Val
            405                 410                 415 cag gct tac aat gta cca gta ggt ccg caa acc ttt tct tta gcg att    1296
Gln Ala Tyr Asn Val Pro Val Gly Pro Gln Thr Phe Ser Leu Ala Ile
            420                 425                 430 gta cat taa                                                         1305
Val His <210> SEQ ID NO 12
<211> LENGTH: 434
<212> TYPE: PRT
<213> ORGANISM: Artificial sequence
<220> FEATURE:
<223> OTHER INFORMATION: Synthetic Construct

<400> SEQUENCE: 12

Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ser Asn Asp
    50                  55                  60

Pro Asn Gly His Gly Thr His Val Ala Gly Ser Val Leu Gly Asn Gly
65                  70                  75                  80

Thr Ser Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Ser
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Ala Val Leu Phe Ala Ala
145                 150                 155                 160

Gly Asn Glu Gly Pro Gly Ser Ser Thr Val Asn Ala Pro Gly Thr Ala
                165                 170                 175

Lys Asn Ala Ile Thr Val Gly Ala Thr Glu Asn Tyr Arg Pro Ser Phe
            180                 185                 190

Gly Ser Tyr Ala Asp Asn Ile Asn His Val Ala Gln Phe Ser Ser Arg
        195                 200                 205

Gly Pro Thr Arg Asp Gly Arg Ile Lys Pro Asp Val Met Ala Pro Gly
```

```
                       210                 215                 220
Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
                260                 265                 270

Ile Lys Asn Arg Gly Ile Thr Pro Lys Pro Ser Leu Leu Lys Ala Ala
                275                 280                 285

Leu Ile Ala Gly Ala Thr Asp Val Gly Leu Gly Phe Pro Asn Gly Asn
290                 295                 300

Gln Gly Trp Gly Arg Val Thr Leu Asp Lys Ser Leu Asn Thr Ala Phe
305                 310                 315                 320

Val Asn Glu Thr Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
                340                 345                 350

Asp Ala Pro Ala Ser Thr Ser Ala Ser Ile Thr Leu Val Asn Asp Leu
                355                 360                 365

Asp Leu Val Ile Thr Ala Pro Asn Gly Thr Gln Tyr Val Gly Asn Asp
    370                 375                 380

Phe Thr Ala Pro Tyr Asn Asn Trp Asp Gly Arg Asn Asn Val Glu
385                 390                 395                 400

Asn Val Phe Ile Asn Ala Pro Gln Ser Gly Thr Tyr Thr Val Glu Val
                405                 410                 415

Gln Ala Tyr Asn Val Pro Val Gly Pro Gln Thr Phe Ser Leu Ala Ile
                420                 425                 430

Val His

<210> SEQ ID NO 13
<211> LENGTH: 1305
<212> TYPE: DNA
<213> ORGANISM: Artificial sequence
<220> FEATURE:
<223> OTHER INFORMATION: JP170/AMRK133 hybrid
<220> FEATURE:
<221> NAME/KEY: CDS
<222> LOCATION: (1)..(1305)

<400> SEQUENCE: 13 aat gac gtg gcc cgt ggc att gtg aaa gca gac gtc gca caa aat aac     48
Asn Asp Val Ala Arg Gly Ile Val Lys Ala Asp Val Ala Gln Asn Asn
1               5                   10                  15 ttt ggc tta tat gga caa gga cag att gta gca gtt gct gat act ggg     96
Phe Gly Leu Tyr Gly Gln Gly Gln Ile Val Ala Val Ala Asp Thr Gly
            20                  25                  30 ctt gat aca gga aga aat gac agt tcg atg cat gaa gca ttc cgc gga    144
Leu Asp Thr Gly Arg Asn Asp Ser Ser Met His Glu Ala Phe Arg Gly
        35                  40                  45 aaa atc act gcc ttg tat gcg tta gga aga tcc aat aat tca aac gat    192
Lys Ile Thr Ala Leu Tyr Ala Leu Gly Arg Ser Asn Asn Ser Asn Asp
    50                  55                  60 ccg aat ggt cat ggt aca cac gtg gct gga tct gtt ctt ggg aac gga    240
Pro Asn Gly His Gly Thr His Val Ala Gly Ser Val Leu Gly Asn Gly
65                  70                  75                  80 gca acg aat aaa ggt atg gcg cca cag gct aat ctt gtc ttc caa tca    288
Ala Thr Asn Lys Gly Met Ala Pro Gln Ala Asn Leu Val Phe Gln Ser
                85                  90                  95
```

```
atc atg gac agc agt ggc gga ttg ggc ggc ctt cct tcc aac ttg agc      336
Ile Met Asp Ser Ser Gly Gly Leu Gly Gly Leu Pro Ser Asn Leu Ser
        100                 105                 110 aca ttg ttc agc caa gct tat agt gcc gga gca aga atc cat acg aat      384
Thr Leu Phe Ser Gln Ala Tyr Ser Ala Gly Ala Arg Ile His Thr Asn
            115                 120                 125 tca tgg ggt gct gcg gta aat ggg gcg tac aca act gat tcc aga aat      432
Ser Trp Gly Ala Ala Val Asn Gly Ala Tyr Thr Thr Asp Ser Arg Asn
130                 135                 140 gtg gat gac tat gtt cgt aaa aat gac atg gca gtc ctt ttc gca gcc      480
Val Asp Asp Tyr Val Arg Lys Asn Asp Met Ala Val Leu Phe Ala Ala
145                 150                 155                 160 ggt aat gaa gga ccg aac agc ggc acc atc agt gca ccg ggt act gcc      528
Gly Asn Glu Gly Pro Asn Ser Gly Thr Ile Ser Ala Pro Gly Thr Ala
                165                 170                 175 aaa aac gcc atc aca gtc gga gcg acg gaa aac tta cgt cca agc ttt      576
Lys Asn Ala Ile Thr Val Gly Ala Thr Glu Asn Leu Arg Pro Ser Phe
                180                 185                 190 gga tcg tat gca gac aac atc aac cat gtt gca cag ttc tct tcc cgc      624
Gly Ser Tyr Ala Asp Asn Ile Asn His Val Ala Gln Phe Ser Ser Arg
            195                 200                 205 gga ccg act cga gac ggt cga atc aag ccg gat gta atg gca cct gga      672
Gly Pro Thr Arg Asp Gly Arg Ile Lys Pro Asp Val Met Ala Pro Gly
210                 215                 220 aca tac att tta tcc gca cgt tca tcc ttg gct cca aac tct tcc ttc      720
Thr Tyr Ile Leu Ser Ala Arg Ser Ser Leu Ala Pro Asn Ser Ser Phe
225                 230                 235                 240 tgg gca aac cat gac agc aaa tat gct tac atg ggc gga act tcc atg      768
Trp Ala Asn His Asp Ser Lys Tyr Ala Tyr Met Gly Gly Thr Ser Met
                245                 250                 255 gca aca ccg att gtt gcc gga aac gtg gca caa tta cgt gag cat ttt      816
Ala Thr Pro Ile Val Ala Gly Asn Val Ala Gln Leu Arg Glu His Phe
                260                 265                 270 atc aaa aac aga gga atc aca cct aag ccg tcg ttg ctg aag gct gcc      864
Ile Lys Asn Arg Gly Ile Thr Pro Lys Pro Ser Leu Leu Lys Ala Ala
            275                 280                 285 ctt atc gca ggt gcc aca gat gtg ggt ctc gga ttc ccg aac ggc aac      912
Leu Ile Ala Gly Ala Thr Asp Val Gly Leu Gly Phe Pro Asn Gly Asn
290                 295                 300 caa ggc tgg ggc cgt gta aca ttg gat aag tca ttg aac aca gca ttt      960
Gln Gly Trp Gly Arg Val Thr Leu Asp Lys Ser Leu Asn Thr Ala Phe
305                 310                 315                 320 gtg aat gag aca agc tca ctg tcc aca agt caa aag gca acg tat tct     1008
Val Asn Glu Thr Ser Ser Leu Ser Thr Ser Gln Lys Ala Thr Tyr Ser
                325                 330                 335 ttt aca gcc act gca ggc aag cca ctt aag atc tct cta gtt tgg tct     1056
Phe Thr Ala Thr Ala Gly Lys Pro Leu Lys Ile Ser Leu Val Trp Ser
                340                 345                 350 gat gct cct gca agt aca tcc gct tct gtg aca tta gtg aat gac ctt     1104
Asp Ala Pro Ala Ser Thr Ser Ala Ser Val Thr Leu Val Asn Asp Leu
            355                 360                 365 gac ttg gtg att act gct cca aac gga acg aaa tat gtt gga aac gac     1152
Asp Leu Val Ile Thr Ala Pro Asn Gly Thr Lys Tyr Val Gly Asn Asp
370                 375                 380 ttc act gca cca ttt gat aac aac tgg gat ggc gcc aac aac gtg gaa     1200
Phe Thr Ala Pro Phe Asp Asn Asn Trp Asp Gly Arg Asn Asn Val Glu
385                 390                 395                 400 aat gtg ttt atc aat gct cct caa agc gga acg tat aca gtc gaa gtg     1248
Asn Val Phe Ile Asn Ala Pro Gln Ser Gly Thr Tyr Thr Val Glu Val
                405                 410                 415
```

```
cag gct tac aat gta cca gta ggt ccg caa acc ttt tct tta gcg att    1296
Gln Ala Tyr Asn Val Pro Val Gly Pro Gln Thr Phe Ser Leu Ala Ile
                420                 425                 430 gta cat taa                                                        1305
Val His

<210> SEQ ID NO 14
<211> LENGTH: 434
<212> TYPE: PRT
<213> ORGANISM: Artificial sequence
<220> FEATURE:
<223> OTHER INFORMATION: Synthetic Construct

<400> SEQUENCE: 14

Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Ser Asn Asn Ser Asn Asp
    50                  55                  60

Pro Asn Gly His Gly Thr His Val Ala Gly Ser Val Leu Gly Asn Gly
65                  70                  75                  80

Ala Thr Asn Lys Gly Met Ala Pro Gln Ala Asn Leu Val Phe Gln Ser
                85                  90                  95

Ile Met Asp Ser Ser Gly Gly Leu Gly Gly Leu Pro Ser Asn Leu Ser
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Ala Val Leu Phe Ala Ala
145                 150                 155                 160

Gly Asn Glu Gly Pro Asn Ser Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Arg Asp Gly Arg Ile Lys Pro Asp Val Met Ala Pro Gly
    210                 215                 220

Thr Tyr Ile Leu Ser Ala Arg Ser Ser Leu Ala Pro Asn Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
        275                 280                 285

Leu Ile Ala Gly Ala Thr Asp Val Gly Leu Gly Phe Pro Asn Gly Asn
    290                 295                 300

Gln Gly Trp Gly Arg Val Thr Leu Asp Lys Ser Leu Asn Thr Ala Phe
305                 310                 315                 320

Val Asn Glu Thr Ser Ser Leu Ser Thr Ser Gln Lys Ala Thr Tyr Ser
                325                 330                 335
```

```
Phe Thr Ala Thr Ala Gly Lys Pro Leu Lys Ile Ser Leu Val Trp Ser
                340                 345                 350

Asp Ala Pro Ala Ser Thr Ser Ala Ser Val Thr Leu Val Asn Asp Leu
            355                 360                 365

Asp Leu Val Ile Thr Ala Pro Asn Gly Thr Lys Tyr Val Gly Asn Asp
370                 375                 380

Phe Thr Ala Pro Phe Asp Asn Asn Trp Asp Gly Arg Asn Asn Val Glu
385                 390                 395                 400

Asn Val Phe Ile Asn Ala Pro Gln Ser Gly Thr Tyr Thr Val Glu Val
                405                 410                 415

Gln Ala Tyr Asn Val Pro Val Gly Pro Gln Thr Phe Ser Leu Ala Ile
            420                 425                 430

Val His

<210> SEQ ID NO 15
<211> LENGTH: 22
<212> TYPE: DNA
<213> ORGANISM: Artificial sequence
<220> FEATURE:
<223> OTHER INFORMATION: Primer SF16A767F
<220> FEATURE:
<221> NAME/KEY: misc_feature
<222> LOCATION: (2)..(2)
<223> OTHER INFORMATION: n in position 2 is inosine
<220> FEATURE:
<221> NAME/KEY: misc_feature
<222> LOCATION: (14)..(14)
<223> OTHER INFORMATION: n in position 14 is inosine

<400> SEQUENCE: 15
cnatgcatga agcnttccgc gg                                          22

<210> SEQ ID NO 16
<211> LENGTH: 21
<212> TYPE: DNA
<213> ORGANISM: Artificial sequence
<220> FEATURE:
<223> OTHER INFORMATION: Primer SF16A1802R
<220> FEATURE:
<221> NAME/KEY: misc_feature
<222> LOCATION: (2)..(2)
<223> OTHER INFORMATION: n in position 2 is inosine
<220> FEATURE:
<221> NAME/KEY: misc_feature
<222> LOCATION: (11)..(11)
<223> OTHER INFORMATION: n in position 11 is inosine
<220> FEATURE:
<221> NAME/KEY: misc_feature
<222> LOCATION: (13)..(13)
<223> OTHER INFORMATION: n in position 13 is inosine

<400> SEQUENCE: 16
cnacgttgtt ncngccatcc c                                           21

<210> SEQ ID NO 17
<211> LENGTH: 24
<212> TYPE: DNA
<213> ORGANISM: Artificial sequence
<220> FEATURE:
<223> OTHER INFORMATION: PD456 PCR Primer Forward

<400> SEQUENCE: 17
aggattcccg aacggaaacc aagg                                        24

<210> SEQ ID NO 18
<211> LENGTH: 23
<212> TYPE: DNA
```

-continued

<213> ORGANISM: Artificial sequence
<220> FEATURE:
<223> OTHER INFORMATION: PD456 PCR Primer Reverse

<400> SEQUENCE: 18
tccgtttcca agtacagacc cgg                                    23

<210> SEQ ID NO 19
<211> LENGTH: 25
<212> TYPE: DNA
<213> ORGANISM: Artificial sequence
<220> FEATURE:
<223> OTHER INFORMATION: JT169 PCR Primer Forward

<400> SEQUENCE: 19
tctctctagt atggtctgat gctcc                                  25

<210> SEQ ID NO 20
<211> LENGTH: 24
<212> TYPE: DNA
<213> ORGANISM: Artificial sequence
<220> FEATURE:
<223> OTHER INFORMATION: JT169 PCR Primer Reverse

<400> SEQUENCE: 20
tccgtttcca agaacagatc cggc                                   24

<210> SEQ ID NO 21
<211> LENGTH: 20
<212> TYPE: DNA
<213> ORGANISM: Artificial sequence
<220> FEATURE:
<223> OTHER INFORMATION: JT169 Forward Sequencing Primer

<400> SEQUENCE: 21
atctgcttct ataacactgg                                        20

<210> SEQ ID NO 22
<211> LENGTH: 20
<212> TYPE: DNA
<213> ORGANISM: Artificial sequence
<220> FEATURE:
<223> OTHER INFORMATION: JT169 Reverse Sequencing Primer 1

<400> SEQUENCE: 22
tgcgttccgt gaccatttgg                                        20

<210> SEQ ID NO 23
<211> LENGTH: 20
<212> TYPE: DNA
<213> ORGANISM: Artificial sequence
<220> FEATURE:
<223> OTHER INFORMATION: JT169 Reverse Sequencing Primer 2

<400> SEQUENCE: 23
tttgcgtcaa gtgccacagc                                        20

<210> SEQ ID NO 24
<211> LENGTH: 20
<212> TYPE: DNA
<213> ORGANISM: Artificial sequence
<220> FEATURE:
<223> OTHER INFORMATION: JT169 Reverse Sequencing Primer 3

<400> SEQUENCE: 24
tcaacaattt catctatgcc                                        20

```
<210> SEQ ID NO 25
<211> LENGTH: 20
<212> TYPE: DNA
<213> ORGANISM: Artificial sequence
<220> FEATURE:
<223> OTHER INFORMATION: PD456  Forward Sequencing Primer

<400> SEQUENCE: 25
gccgtgtaac aatggacaag                                              20

<210> SEQ ID NO 26
<211> LENGTH: 20
<212> TYPE: DNA
<213> ORGANISM: Artificial sequence
<220> FEATURE:
<223> OTHER INFORMATION: PD456  Reverse Sequencing Primer 1

<400> SEQUENCE: 26
tccctttatt ggttgctccg                                              20

<210> SEQ ID NO 27
<211> LENGTH: 22
<212> TYPE: DNA
<213> ORGANISM: Artificial sequence
<220> FEATURE:
<223> OTHER INFORMATION: Primer PEP192

<400> SEQUENCE: 27
ccgcggaatg cttcatgcat cg                                           22

<210> SEQ ID NO 28
<211> LENGTH: 30
<212> TYPE: DNA
<213> ORGANISM: Artificial sequence
<220> FEATURE:
<223> OTHER INFORMATION: Primer PEP200

<400> SEQUENCE: 28
gttcatcgat cttctactat tggggcgaac                                   30

<210> SEQ ID NO 29
<211> LENGTH: 21
<212> TYPE: DNA
<213> ORGANISM: Artificial sequence
<220> FEATURE:
<223> OTHER INFORMATION: Primer PEP193

<400> SEQUENCE: 29
gggatggcag aaacaacgtg g                                            21

<210> SEQ ID NO 30
<211> LENGTH: 35
<212> TYPE: DNA
<213> ORGANISM: Artificial sequence
<220> FEATURE:
<223> OTHER INFORMATION: Primer PEP201

<400> SEQUENCE: 30
ttaaacgcgt ttaatgtaca atcgctaaag aaaag                             35

<210> SEQ ID NO 31
<211> LENGTH: 32
<212> TYPE: DNA
<213> ORGANISM: Artificial sequence
<220> FEATURE:
<223> OTHER INFORMATION: JT169 Expression Forward Primer
```

-continued

```
<400> SEQUENCE: 31
agttcatcga tcgggggagc tagcagcttc ga                          32

<210> SEQ ID NO 32
<211> LENGTH: 32
<212> TYPE: DNA
<213> ORGANISM: Artificial sequence
<220> FEATURE:
<223> OTHER INFORMATION: JT169 Expression Reverse Primer

<400> SEQUENCE: 32
tgattaacgc gtttagttca caatcgccaa tg                          32

<210> SEQ ID NO 33
<211> LENGTH: 32
<212> TYPE: DNA
<213> ORGANISM: Artificial sequence
<220> FEATURE:
<223> OTHER INFORMATION: PD456 Expression Forward Primer

<400> SEQUENCE: 33
agttcatcga tcgggggggc tagcaacttt ga                          32

<210> SEQ ID NO 34
<211> LENGTH: 32
<212> TYPE: DNA
<213> ORGANISM: Artificial sequence
<220> FEATURE:
<223> OTHER INFORMATION: PD456 Expression Reverse Primer

<400> SEQUENCE: 34
tgattaacgc gtttagttca caatcgccaa tg                          32
```

SUBTILASES

CROSS-REFERENCE TO RELATED APPLICATIONS

This application is a divisional of U.S. application Ser. No. 12/879,156 filed on Sep. 10, 2010 (now U.S. Pat. No. 7,910,349), which is a divisional of U.S. application Ser. No. 11/575,551 filed on Mar. 19, 2007 (now U.S. Pat. No. 7,816,115) which is a 35 U.S.C. 371 national application of PCT/DK2005/000597 filed Sep. 21, 2005, which claims priority or the benefit under 35 U.S.C. 119 of Danish application no. PA 2004 01429 filed Sep. 21, 2004 and U.S. provisional application No. 60/611,720 filed Sep. 21, 2004, the contents of which are fully incorporated herein by reference.

SEQUENCE LISTING AND DEPOSITED MICROORGANISMS

Sequence Listing

The present invention comprises a sequence listing, which is fully incorporated herein by reference.
Deposit of Biological Material
The following biological material has been deposited under the terms of the Budapest Treaty with Deutsche Sammlung von Mikroorganismen and Zellkulturen and given the following accession numbers:

| Deposit | Accession Number | Date of Deposit |
| --- | --- | --- |
| JP170/PD456 hybrid | DSM16714 | 15 Sep. 2004 |
| JP170/JT169 hybrid | DSM16715 | 15 Sep. 2004 |
| JT169 | DSM16719 | 15 Sep. 2004 |
| PD456 | DSM16722 | 15 Sep. 2004 |
| JP170/JP75 hybrid | DSM16712 | 15 Sep. 2004 |
| JP170/JP40 hybrid | DSM16713 | 15 Sep. 2004 |
| JP170/AMRK133 hybrid | DSM16716 | 15 Sep. 2004 |

The deposits contain subtilase genes and hybrid subtilase genes as described in example 1-3.

FIELD OF THE INVENTION

The present invention relates to novel JP170 like subtilases from wild-type bacteria, hybrids thereof and to methods of construction and production of these proteases. Further, the present invention relates to use of the claimed subtilases in detergents, such as a laundry detergent or an automatic dishwashing detergent.

BACKGROUND OF THE INVENTION

Enzymes have been used within the detergent industry as part of washing formulations for more than 30 years. Proteases are from a commercial perspective the most relevant enzyme in such formulations, but other enzymes including lipases, amylases, cellulases, hemicellulases or mixtures of enzymes are also often used.

The search for proteases with appropriate properties include both discovery of naturally occurring proteases, i.e. so called wild-type proteases but also alteration of well-known proteases by e.g. genetic manipulation of the nucleic acid sequence encoding said proteases. One family of proteases, which is often used in detergents, is the subtilases. This family has been further grouped into 6 different subgroups (Siezen R. J. and Leunissen J. A. M., 1997, Protein Science, 6, 501-523). One of these sub-groups, the Subtilisin family was further divided into the subgroups of "true subtilisins (I-S1)", "high alkaline proteases (I-S2)" and "intracellular proteases". Siezen and Leunissen identified also some proteases of the subtilisin family, but not belonging to any of the subgroups. The true subtilisins include proteases such as subtilisin BPN' (BASBPN), subtilisin Carlsberg (ALCALASE®, NOVOZYMES A/S) (BLSCAR), mesentericopeptidase (BMSAMP) and subtilisin DY (BSSDY). The high alkaline proteases include proteases such as subtilisin 309 (SAVINASE®, NOVOZYMES A/S) (BLSAVI) subtilisin PB92 (BAALKP), subtilisin BL or BLAP (BLSUBL), subtilisin 147 (ESPERASE®, NOVOZYMES A/S), subtilisin Sendai (BSAPRS) and alkaline elastase YaB. Outside this grouping of the subtilisin family a further subtilisin subgroup was recently identified on the basis of the 3-D structure of its members, the TY145 like subtilisins. The TY145 like subtilisins include proteases such as TY145 (a subtilase from Bacillus sp. TY145, NCIMB 40339 described in WO 92/17577) (BSTY145), subtilisin TA41 (BSTA41), and subtilisin TA39 (BSTA39).

The JP170 subtilase type was first described as protease A in WO 88/01293 to Novozymes A/S disclosing four strains producing this type of protease. Later U.S. Pat. No. 5,891,701 to Novozymes Biotech disclosed the amino acid sequence of JP170 and the DNA sequence encoding it. The patents JP7-62152 and JP 4197182 to Lion Corp. disclosed the alkaline protease Yb produced by Bacillus sp. Y that is homologous to JP170 and the DNA sequence encoding Yb. Bacillus sp. Y also produces the protease Ya (Geneseq P entry AAR26274). And in addition U.S. Pat. No. 6,376,227 to Kao Corp. discloses physical characteristics as well as DNA and polypeptide sequences of alkaline proteases KP43, KP1790 and KP9860 which are also homologous to JP170. Recently genetic engineered variants of the KP43, KP9860 and Ya proteases among others were disclosed in EP 1 209 233, which also disclosed protease A-2 from Bacillus sp. NCIB12513. Kao Corp. also disclosed the proteases KSM-KP9865 and A-1 in US 2004/072321. Other known proteases belonging to this group are Protease E-1 derived from Bacillus sp. strain No. D6 (FERM P-1592), JP7407101, Protease SD521 derived from Bacillus sp. strain SD-521 (FERM BP-11162), JP9108211, and protease A1 derived from NCIB12289, WO 88/01293 to Novozymes NS.

BRIEF DESCRIPTION OF THE INVENTION

The inventors have isolated novel proteases belonging to the JP170 like proteases subgroup of the subtilisin family that possess advantageous properties, such as improved detergent stability.

Furthermore the inventors have inserted truncated forms of the genes encoding various members of this subgroup into the gene encoding the JP170 protease thereby creating hybrid JP170 like proteases exhibiting improved performance in comparison to the JP170 protease.

The invention therefore in a further embodiment provides hybrid proteases.

BRIEF DESCRIPTION OF DRAWINGS

FIG. 2, Matrix with amino acid sequence identities of the enzymes of the invention and the closest prior art known to the applicant.

DEFINITIONS

Figure 1:
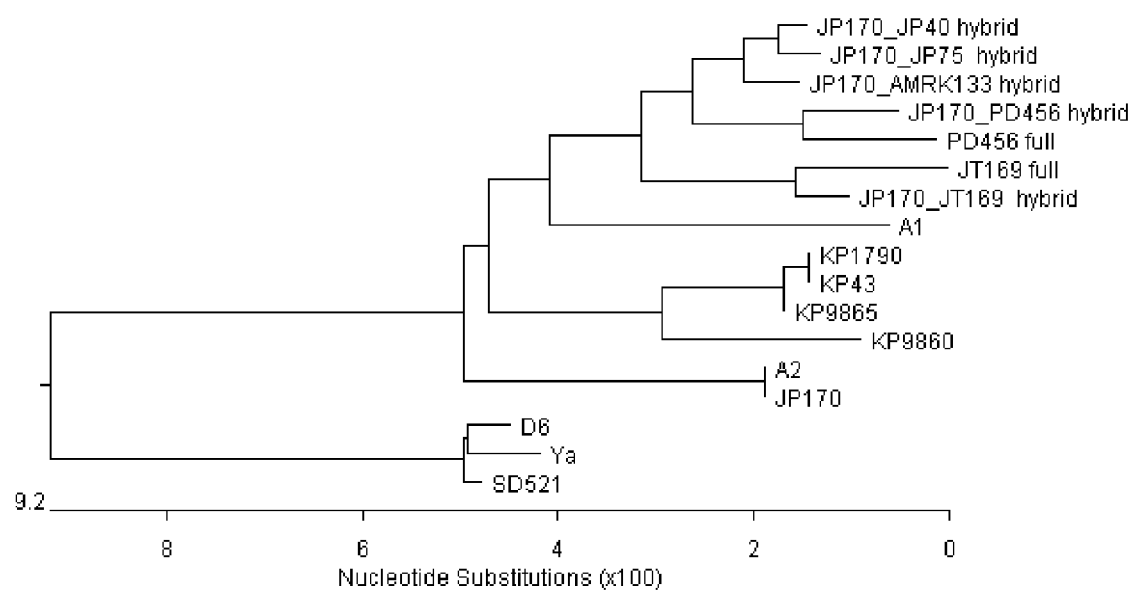
FIG. 1, Phylogenetic tree showing the relationship of the mature subtilase peptide sequences were constructed upon alignment with default settings in the ClustalW function of program MegAlign™ version 5.05 in DNAStar™ program package.

Prior to discussing this invention in further detail, the following terms and conventions will first be defined.

For a detailed description of the nomenclature of amino acids and nucleic acids, we refer to WO 00/71691 page 5, hereby incorporated by reference. A description of the nomenclature of modifications introduced in a polypeptide by genetic manipulation can be found in WO 00/71691 page 7-12, hereby incorporated by reference.

The term "subtilases" refer to a sub-group of serine proteases according to Siezen et al., *Protein Engng.* 4 (1991) 719-737 and Siezen et al. *Protein Science* 6 (1997) 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue.

The subtilases may be divided into 6 sub-divisions, i.e. the Subtilisin family, the Thermitase family, the Proteinase K family, the Lantibiotic peptidase family, the Kexin family and the Pyrolysin family.

The Subtilisin family (EC 3.4.21.62) may be further divided into 3 sub-groups, i.e. I-S1 ("true" subtilisins), I-S2 (highly alkaline proteases) and intracellular subtilisins. Definitions or grouping of enzymes may vary or change, however, in the context of the present invention the above division of subtilases into sub-division or sub-groups shall be understood as those described by Siezen et al., *Protein Engng.* 4 (1991) 719-737 and Siezen et al. *Protein Science* 6 (1997) 501-523.

The term "parent" is in the context of the present invention to be understood as a protein, which is modified to create a protein variant. The parent protein may be a naturally occurring (wild-type) polypeptide or it may be a variant thereof prepared by any suitable means. For instance, the parent protein may be a variant of a naturally occurring protein which has been modified by substitution, chemical modification, deletion or truncation of one or more amino acid residues, or by addition or insertion of one or more amino acid residues to the amino acid sequence, of a naturally-occurring polypeptide. Thus the term "parent subtilase" refers to a subtilase which is modified to create a subtilase variant.

The term "hybrid" is in the context of this invention to be understood as a protein that has been modified by replacing one or more segments of the gene encoding the parent protein with corresponding segments derived from genes encoding another protein.

The term "core" in the context of this invention is to be understood as a segment that comprises a substantial part of the subtilase gene including the part encoding the active site and a substantial part of the rest of the subtilase molecule, to provide unique traits to a hybrid.

The term "modification(s)" or "modified" is in the context of the present invention to be understood as to include chemical modification of a protein as well as genetic manipulation of the DNA encoding a protein. The modification(s) may be replacement(s) of the amino acid side chain(s), substitution(s), deletion(s) and/or insertions in or at the amino acid(s) of interest. Thus the term "modified protein", e.g. "modified subtilase", is to be understood as a protein which contains modification(s) compared to a parent protein, e.g. subtilase.

"Homology" or "homologous to" is in the context of the present invention to be understood in its conventional meaning and the "homology" between two amino acid sequences should be determined by use of the "Similarity" defined by the GAP program from the University of Wisconsin Genetics Computer Group (UWGCG) package using default settings for alignment parameters, comparison matrix, gap and gap extension penalties. Default values for GAP penalties, i.e. GAP creation penalty of 3.0 and GAP extension penalty of 0.1 (Program Manual for the Wisconsin Package, Version 8, August 1994, Genetics Computer Group, 575 Science Drive, Madison, Wis., USA 53711). The method is also described in S. B. Needleman and C. D. Wunsch, Journal of Molecular Biology, 48, 443-445 (1970). Identities can be extracted from the same calculation. The homology between two amino acid sequences can also be determined by "identity" or "similarity" using the GAP routine of the UWGCG package version 9.1 with default setting for alignment parameters, comparison matrix, gap and gap extension penalties can also be applied using the following parameters: gap creation penalty=8 and gap extension penalty=8 and all other parameters kept at their default values. The output from the routine is besides the amino acid alignment the calculation of the "Percent Identity" and the "Similarity" between the two sequences. The numbers calculated using UWGCG package version 9.1 is slightly different from the version 8.

The term "position" is in the context of the present invention to be understood as the number of an amino acid in a peptide or polypeptide when counting from the N-terminal end of said peptide/polypeptide. The position numbers used in the present invention refer to different subtilases depending on which subgroup the subtilase belongs to.

DETAILED DESCRIPTION OF THE INVENTION

Construction of Degenerated Primers

Degenerated primers were constructed from an alignment of genes of already known proteases such as Ya, KAO KSM-43 and JP170. The primers were degenerated in order to allow screening for protease gene fragments different from Ya, KAO KSM-43 and JP170.

PCR Screening

From the company culture collection a selection of bacterial strains were included in a PCR screening using the primers SF16A767F and SF16A1802R. The expected size of the PCR product was 1050 nucleotides. All PCR products of the expected size were sequenced in two sequence reaction using one of each of the same two primers. The nucleotide sequences were translated to amino acid sequences, and the diversity analysed by comparative peptide sequence analysis.

Based on the results of the screening a number of enzymes were selected for further investigation. The selected enzymes are shown in FIG. 1, and they both represent new enzyme molecules and representatives of the prior art. The enzymes selected for further investigation are JP40, JP75, JT169, AMRK133 and PD456, which can be seen as forming a separate group in FIG. 1. Also hybrid subtilases produced as described below can be seen in FIG. 1.

Based on these results the inventors decided to move on with a dual approach; expression of the PCR product by in frame fusions to N and C terminal parts of the known protease of *Bacillus halmapalus* strain JP170 and inverse PCR to get the full sequences of selected enzymes.

Expression of Hybrid Proteases

Description of SOE PCR

By SOE PCR(SOE: Splicing by Overlapping Extension) hybrid gene products comprising 5 segments were generated as described in Example 2. The hybrid subtilase genes are used for production of a mature protease enzyme of about 433 amino-acids and a molecular weight of approximately 45 kd. The first segment is the nucleotide sequence encoding the pro sequence of JP170 protease (that is not a part of the mature protease) and 40 amino acids of the N terminal of the mature JP170 protease. This is followed by a fusion primer segment encoding 8 amino acids (this segment may contain sequence variation due to the degeneration of the primer SF16A767F). The third segment is encoding the approximately 343 amino acid long core. This segment includes the sequence encoding the active site of the protease. This is followed by a fusion primer segment encoding 7 amino acids (this segment may contain variation due to the degeneration of the primer SF16A1802R). The fifth segment is encoding the 35 amino acids of the C terminal of the JP170 protease.

SOE PCR products based on core segments from the following strains were generated: JP40 (SEQ ID NO:5), PD456 (SEQ ID NO:7), JP75 (SEQ ID NO:9), JT169 (SEQ ID NO:11), AMRK133 (SEQ ID NO:13) (the SEQ ID number of the gene sequence encoding the mature hybrid protease is indicated in brackets).

The core of the subtilase of the invention may comprise 50-420 amino acid residues, preferably 50-100 amino acid residues, 100-150 amino acid residues, 150-200 amino acid residues 200-250 amino acid residues, 250-300 amino acid residues, 300-350 amino acid residues, 350-400 amino acid residues, 400-420 amino acid residues. Especially preferred is a core segment comprising approximately 343 amino acid residues.

The N terminal end of the core segment is located in one of positions 1-10, 10-20, 20-30, 30-40, 40-50, 50-60 or 60-70 of the subtilase of SEQ ID NO:6, SEQ ID NO:8, SEQ ID NO:10, SEQ ID NO:12 or SEQ ID NO:14. The C terminal end of the core segment is located in one of positions 70-80, 80-90, 90-100, 100-150, 150-200, 200-250, 250-300, 300-320, 320-340, 340-360, 360-380, 380-400, 400-420 of the subtilase of SEQ ID NO:6, SEQ ID NO:8, SEQ ID NO:10, SEQ ID NO:12 or SEQ ID NO:14. In a preferred embodiment the core of the subtilase of the invention comprises the amino acids in position 49-392 of the hybrids JP40 (SEQ ID NO:6), PD456 (SEQ ID NO:8), JP75 (SEQ ID NO:10), JT169 (SEQ ID NO:12), AMRK133 (SEQ ID NO:14).

The core sequence preferably has 94% identity with the amino acids in position 49-392 of SEQ ID NO:6, SEQ ID NO:8, SEQ ID NO:10, SEQ ID NO:12 or SEQ ID NO:14. More preferably the core sequence has 95% identity, 96% identity, 97% identity, 98% identity or 99% identity with SEQ ID NO:6, SEQ ID NO:8, SEQ ID NO:10, SEQ ID NO:12 or SEQ ID NO:14.

The corresponding nucleotides encoding the core segment can be seen in any of SEQ ID NO:5, SEQ ID NO:7, SEQ ID NO:9, SEQ ID NO:11 or SEQ ID NO:13. In a preferred embodiment the core of the subtilase of the invention is encoded by the nucleotides in position 145-1177 of the hybrids JP40 (SEQ ID NO:5), PD456 (SEQ ID NO:7), JP75 (SEQ ID NO:9), JT169 (SEQ ID NO:11), AMRK133 (SEQ ID NO:13).

The N and C terminals of the hybrids of the present invention could equally well be selected from other subtilases, such as BLSCAR, BMSAMP, BASBPN or BSSDY of 1-S1, BLSAVI, BAALKP, BLSUBL or subtilisin 147 of 1-S2, a members of the TY145 like subtilases, or another member of the JP170 like subtilases.

The lengths of the N and C terminal sequences vary from 1 to approximately 150 amino acid residues. Preferably the length of the terminals are 1-20 amino acid residues, 20-40 amino acid residues, 40-60 amino acid residues, 60-80 amino acid residues, 80-100 amino acid residues, 100-120 amino acid residues, 120-150 amino acid residues.

The subtilase hybrids of the invention are preferable produced by use of the fusion primers described in Example 2, but other suitable primers may equally well be used.

Cloning of the Hybrid Protease

The PCR fragment was cloned into plasmid pDG268NeoMCS-PramyQ/PrcryIII/cryIIIAstab/Sav (U.S. Pat. No. 5,955,310) and transformed in *Bacillus subtilis*. Protease positive colonies were selected and the coding sequence of the expressed enzyme from the expression construct was confirmed by DNA sequence analysis.

Cloning and Expression of Full Length Subtilase of the Invention

Inverse PCR

Inverse PCR was performed with specific DNA primers designed to complement the DNA sequence of the core PCR product and chromosomal DNA extracted from the appropriate bacterial strain. Inverse PCR was made on the strains JT169 and PD456. The inverse PCR products were nucleotide sequenced to obtain the region encoding the N and C terminal parts of the gene.

Production of Full Length Subtilase

The subtilase genes were amplified with specific primers with restriction sites in the 5' end of primers that allow gene fusion with the Savinase signal peptide of plasmid pDG268NeoMCS-PramyQ/PrcryIII/cryIIIAstab/Sav (U.S. Pat. No. 5,955,310). Protease positive colonies were selected and the coding sequence of the expressed enzyme from the expression construct was confirmed by DNA sequence analysis.

Subtilases of the Invention

The subtilase is in the context of the present invention to be understood as including the members of the novel subgroup of FIG. 1: JP40, PD456, JP75, JT169, AMRK133 and homologous or hybrids thereof. According to the identity matrix of FIG. 2 the amino acid sequence identity of the closest related prior art subtilase is 94.7%.

Thus, the subtilase of the present invention is at least 95% identical with SEQ ID NO:2, SEQ ID NO:4, SEQ ID NO:6, SEQ ID NO:8, SEQ ID NO:10, SEQ ID NO:12 or SEQ ID NO:14. In particular said subtilase may be at least 96%, at least 97%, at least 98% or at least 99% identical with SEQ ID NO:2, SEQ ID NO:4, SEQ ID NO:6, SEQ ID NO:8, SEQ ID NO:10, SEQ ID NO:12 or SEQ ID NO:14.

The subtilase of the present invention is encoded by an isolated nucleic acid sequence, which nucleic acid sequence has at least 85% identity with SEQ ID NO:1, SEQ ID NO:3, SEQ ID NO:5, SEQ ID NO:7, SEQ ID NO:9, SEQ ID NO:11 or SEQ ID NO:13. Preferably, said nucleic acid sequence has at least 86%, at least 87%, at least 88%, at least 89%, at least 90%, at least 91%, at least 92%, at least 93%, at least 94%, at least 95%, at least 96%, at least 97%, at least 98%, or at least 99% identity with the nucleic acid sequence shown in SEQ ID NO:1, SEQ ID NO:3, SEQ ID NO:5, SEQ ID NO:7, SEQ ID NO:9, SEQ ID NO:11 or SEQ ID NO:13.

Further the isolated nucleic acid sequence encoding a subtilase of the invention hybridizes with a complementary strand of the nucleic acid sequence shown in SEQ ID NO:1, SEQ ID NO:3, SEQ ID NO:5, SEQ ID NO:7, SEQ ID NO:9, SEQ ID NO:11 or SEQ ID NO:13 preferably under low stringency conditions, at least under medium stringency conditions, at least under medium/high stringency conditions, at least under high stringency conditions, at least under very high stringency conditions.

Hybridization

Suitable experimental conditions for determining hybridization between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 μg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6-13), $^{32}$P-dCTP-labeled (specific activity>1×10$^9$ cpm/μg) probe for 12 hours at ca. 45° C. For various stringency conditions the filter is then washed twice for 30 minutes in 2×SSC, 0.5% SDS and at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

Variants

Combined Modifications

The present invention also encompasses any of the above mentioned subtilase variants in combination with any other modification to the amino acid sequence thereof. Especially combinations with other modifications known in the art to provide improved properties to the enzyme are envisaged.

Such combinations comprise the positions: 222 (improves oxidation stability), 218 (improves thermal stability), substitutions in the Ca$^{2+}$-binding sites stabilizing the enzyme, e.g. position 76, and many other apparent from the prior art.

In further embodiments a subtilase variant described herein may advantageously be combined with one or more modification(s) in any of the positions:
27, 36, 56, 76, 87, 95, 96, 97, 98, 99, 100, 101, 102, 103, 104, 120, 123, 159, 167, 170, 206, 218, 222, 224, 232, 235, 236, 245, 248, 252 and 274 (BPN' numbering).

Specifically, the following BLSAVI, BLSUBL, BSKSMK, and BAALKP modifications are considered appropriate for combination:
K27R, *36D, S56P, N76D, S87N, G97N, S101G, S103A, V104A, V104I, V104N, V104Y, H120D, N123S, G159D, Y167, R170, Q206E, N218S, M222S, M222A, T224S, A232V, K235L, Q236H, Q245R, N248D, N252K and T274A.

Furthermore variants comprising any of the modifications S101G+V104N, S87N+S101G+V104N, K27R+V104Y+N123S+T274A, N76D+S103A+V104I or N76D+V104A, or other combinations of the modifications K27R, N76D, S101G, S103A, V104N, V104Y, V104I, V104A, N123S, G159D, A232V, Q236H, Q245R, N248D, N252K, T274A in combination with any one or more of the modification(s) mentioned above exhibit improved properties.

A particular interesting variant is a variant, which, in addition to modifications according to the invention, contains the following substitutions:
S101G+S103A+V104I+G159D+A232V+Q236H+Q245R+N248D+N252K.

Moreover, subtilase variants of the main aspect(s) of the invention are preferably combined with one or more modification(s) in any of the positions 129, 131 and 194, preferably as 129K, 131H and 194P modifications, and most preferably as P129K, P131H and A194P modifications. Any of those modification(s) are expected to provide a higher expression level of the subtilase variant in the production thereof.

Methods for Expression and Isolation of Proteins

To express an enzyme of the present invention the above mentioned host cells transformed or transfected with a vector comprising a nucleic acid sequence encoding an enzyme of the present invention are typically cultured in a suitable nutrient medium under conditions permitting the production of the desired molecules, after which these are recovered from the cells, or the culture broth.

The medium used to culture the host cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media may be prepared using procedures known in the art (see, e.g., references for bacteria and yeast; Bennett, J. W. and LaSure, L., editors, More Gene Manipulations in Fungi, Academic Press, CA, 1991).

If the enzymes of the present invention are secreted into the nutrient medium, they may be recovered directly from the medium. If they are not secreted, they may be recovered from cell lysates. The enzymes of the present invention may be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the enzyme in question.

The enzymes of the invention may be detected using methods known in the art that are specific for these proteins. These detection methods include use of specific antibodies, formation of a product, or disappearance of a substrate. For example, an enzyme assay may be used to determine the activity of the molecule. Procedures for determining various kinds of activity are known in the art.

The enzymes of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J-C Janson and Lars Ryden, editors, VCH Publishers, New York, 1989).

When an expression vector comprising a DNA sequence encoding an enzyme of the present invention is transformed/transfected into a heterologous host cell it is possible to enable heterologous recombinant production of the enzyme. An advantage of using a heterologous host cell is that it is possible to make a highly purified enzyme composition, characterized in being free from homologous impurities, which are often present when a protein or peptide is expressed in a homologous host cell. In this context homologous impurities mean any impurity (e.g. other polypeptides than the enzyme of the invention) which originates from the homologous cell where the enzyme of the invention is originally obtained from.

Detergent Applications

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations, especially for automatic dish washing (ADW).

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, Renozyme® and Carezyme™ (Novozymes A/S), Clazinase™, and Puradax HA™ (Genencor International Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 which is hereby incorporated as reference.

Typical powder detergent compositions for automated dishwashing include:

1)

| | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

2)

| | |
|---|---|
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dehydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer | 6-25% |
| (e.g. maleic acid/acrylic acid copolymer) | |
| Enzymes | 0.0001-0.1% |
| Perfume | 0.1-0.5% |
| Water | 5-10 |

3)

| | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

4)

| | |
|---|---|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

5)

| | |
|---|---|
| Nonionic surfactant | 1-7% |
| Sodium disilicate | 18-30% |

| | |
|---|---|
| Trisodium citrate | 10-24% |
| Sodium carbonate | 12-20% |
| Monopersulphate (2 $KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

Powder and liquid dishwashing compositions with cleaning surfactant system typically include the following ingredients:

6)

| | |
|---|---|
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |

Non-aqueous liquid automatic dishwashing compositions typically include the following ingredients:

7)

| | |
|---|---|
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

8)

| | |
|---|---|
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

Thixotropic liquid automatic dishwashing compositions typically include the following ingredients:

9)

| | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

Liquid automatic dishwashing compositions typically include the following ingredients:

10)

| | |
|---|---|
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

Liquid automatic dishwashing compositions containing protected bleach particles typically include the following ingredients:

11)

| | |
|---|---|
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

12) Automatic dishwashing compositions as described in 1), 2), 3), 4), 6) and 10), wherein perborate is replaced by percarbonate.

13) Automatic dishwashing compositions as described in 1)-6) which additionally contain a manganese catalyst. The manganese catalyst may, e.g., be one of the compounds described in "Efficient manganese catalysts for low-temperature bleaching", *Nature* 369, 1994, pp. 637-639.

Materials and Methods

Method for Producing a Subtilase Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention. Thereby it is possible to make a highly purified subtilase composition, characterized in being free from homologous impurities.

The medium used to culture the transformed host cells may be any conventional medium suitable for growing the host cells in question. The expressed subtilase may conveniently be secreted into the culture medium and may be recovered there-from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

EXAMPLE 1

PCR Screening

The core part of protease gene was amplified in a PCR reaction that included 50 U/ml of Ampli-taq™ DNA polymerase (Perkin Elmer) 10× Amplitaq buffer (final concentration of $MgCl_2$ is 1.5 mM) 0.2 mM of each of the dNTPs (dATP, dCTP, dTTP and dGTP) 0.2 pmol/µl of the primers SF16A767F (CNATGCATGAAGCNTTCCGCGG, SEQ ID NO:15) ("N" is degeneration introduced by insertion of inosine)) and SF16A1802R(CNACGTTGTTNCNGC-CATCCC, SEQ ID NO:16) and 1 µl template DNA. Template DNA was recovered from the various *Bacillus* strains using HighPure™ PCR template preparation kit (Boehringer Mannheim art. 1796828) as recommended by the manufacturer for DNA recovery from bacteria. The quality of the isolated template was evaluated by agarose gel electrophoresis. If a high molecular weight band was present the quality was accepted. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 1050 nucleotides. The PCR product was recovered by using Qiagen™ PCR purification kit as recommended by the manufacturer. The nucleotide sequences were determined by sequencing on an ABI PRISM™ DNA sequencer (Perkin Elmer). PCR products of PD456, JT169, JP40, JP75 and AMRK133 were determined. The nucleotide sequences were translated to amino acid sequences, and the diversity analysed by comparative peptide sequence analysis. As can be seen in FIG. 1 the diversity by far exceeded that of the prior art.

EXAMPLE 2

Production of Subtilase Hybrids

Expression of Hybrid Proteases, PCR Amplification

In order to produce an active subtilase based on the nucleotide sequence information of the partial sequencing of Example 1, the core PCR product was fused to the N and C terminal parts of the JP170 protease gene in a SOE PCR(SOE: Splicing by Overlapping Extension) reaction as described above. In the SOE PCR reaction a fusion of three PCR products are produced. The three PCR products are:

1) The N terminal part of JP170 protease gene. This PCR product is obtained by PCR using the primers PEP192 5'-CCGCGGAATGCTTCATGCATCG-3' (SEQ ID NO:27) and PEP200 5'-GTTCATCGATCTTCTACTAT-TGGGGCGAAC-3' (SEQ ID NO:28) and 1 µl template DNA. Template DNA was recovered from the various *Bacillus* strains using HighPure™ PCR template preparation kit (Boehringer Mannheim art. 1796828) as recommended by the manufacturer for DNA recovery from bacteria. The quality of the isolated template was evaluated by agarose gel electrophoresis. If a high molecular weight band was present the quality was accepted. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 700 nucleotides.

2) The C terminal part of JP170 protease gene. This PCR product is obtained by PCR using the primers PEP193 5'-GGGATGGCAGAAACAACGTGG-3' (SEQ ID NO:29) and PEP201 5'-TTAAACGCGTTTAATGTA-CAATCGCTAAAGAAAAG-3' (SEQ ID NO:30) and 1 µl template DNA. Template DNA was recovered from the various *Bacillus* strains using HighPure™ PCR template preparation kit (Boehringer Mannheim art. 1796828) as recommended by the manufacturer for DNA recovery from bacteria. The quality of the isolated template was evaluated by agarose gel electrophoresis. If a high molecular weight band was present the quality was accepted. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 370 nucleotides.

3) The core PCR product described in Example 1.

In the SOE PCR reaction the three PCR products are mixed and a fused product is amplified in a standard PCR protocol using the primers PEP200 and PEP201 and 1 µl template DNA. Template DNA is a mixture of the three PCR products described above (1-3). These PCR products may be recovered using Qiaquick™ spin columns as recommended (Qiagen, Germany). The quality of the isolated template was evaluated by agarose gel electrophoresis. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 1850 nucleotides.

The digested and purified PCR fragment was ligated to the Cla I and Mlu I digested plasmid pDG268NeoMCS-PramyQ/PrcryIII/cryIIIAstab/Sav (U.S. Pat. No. 5,955,310).

The ligation mixture was used for transformation into *E. coli* TOP10F' (Invitrogen BV, The Netherlands) and several colonies were selected for miniprep (QIAprep® spin, QIAGEN GmbH, Germany). The purified plasmids were checked for insert before transformation into a strain of *Bacillus subtilis* derived from *B. subtilis* DN 1885 with disrupted apr, npr and pel genes (Diderichsen et al (1990), J. Bacteriol., 172, 4315-4321). The disruption was performed essentially as described in "*Bacillus subtilis* and other Gram-Positive Bacteria," American Society for Microbiology, p. 618, eds. A. L. Sonenshein, J. A. Hoch and Richard Losick (1993). Transformed cells were plated on 1% skim milk LB-PG agar plates, supplemented with 6 μg/ml chloramphenicol. The plated cells were incubated over night at 37° C. and protease containing colonies were identified by a surrounding clearing zone. Protease positive colonies were selected and the coding sequence of the expressed enzyme from the expression construct was confirmed by DNA sequence analysis.

EXAMPLE 3

Production of Full Length Subtilases

Inverse PCR

Three digestions of the chromosomal DNA of the strains PD456 and JT169 were made using the restriction enzymes xho1, BamH1 and Pst1. Upon digestion the DNA was separated from the restriction enzymes using Qiaquick™ PCR purification kit (art. 28106, Qiagen, Germany). The digestions were religated and subjected to a PCR reaction using primers (PCR primers SEQ ID NO:17-20) designed to recognise the sequence of the PCR product already obtained. The following PCR protocols were applied: 94° C. 2 min 30 cycles of [94° C. for 15 s, 52° C. for 30 s, 72° C. for 2 min] 72° C. 20 min. Using same PCR amount of primer polymerase and buffer as above. Alternatively a protocol with 94° C. 2 min 30 cycles of [94° C. for 15 s, 52° C. for 30 s, 68° C. for 3 min] 68° C. 20 min. and replacing Amplitaq® and Amplitaq® buffer with Long-template Taq Polymerase™ (Boehringer Mannheim) with the buffer supplied with the polymerease. The PCR reactions were analysed on 0.8% agarose gels stained with ethidium bromide. All PCR fragments were recovered and the nucleotide sequence was determined by using specific oligo primers different from those used in the PCR reaction (Sequencing primers SEQ ID NO:21-26). In some cases the first primer did not give sufficient nucleotide sequence information to characterise the entire open reading frame of the protease gene. In these cases new primers were applied either by using the sequence information obtained with the initial inverse PCR sequencing primer, or by going back to the initial PCR fragment and defining a new primer sequence.

The following primers were used for obtaining the inverse PCR and sequencing:
PCR Primers

```
PD456 PCR Forward:
AGGATTCCCGAACGGAAACCAAGG        (SEQ ID NO: 17)

PD456 PCR Reverse:
TCCGTTTCCAAGTACAGACCCGG         (SEQ ID NO: 18)

JT169 PCR Forward:
TCTCTCTAGTATGGTCTGATGCTCC       (SEQ ID NO: 19)

JT169 PCR Reverse:
TCCGTTTCCAAGAACAGATCCGGC        (SEQ ID NO: 20)
```

Sequencing Primers

```
JT169 Forward Sequencing
ATCTGCTTCTATAACACTGG            (SEQ ID NO: 21)

JT169 Reverse Sequencing1
TGCGTTCCGTGACCATTTGG            (SEQ ID NO: 22)

JT169 Reverse Sequencing2
TTTGCGTCAAGTGCCACAGC            (SEQ ID NO: 23)

JT169 Reverse Sequencing3
TCAACAATTTCATCTATGCC            (SEQ ID NO: 24)

PD456 Forward Sequencing
GCCGTGTAACAATGGACAAG            (SEQ ID NO: 25)

PD456 Reverse Sequencing1
TCCCTTTATTGGTTGCTCCG            (SEQ ID NO: 26)
```

The gene sequences encoding the mature part of the protease gene of strains JT169 and PD456 are shown in SEQ ID NO:1 and SEQ ID NO:3 respectively.

Production of the Full Length Subtilase

To produce the subtilases of strain JT169 and PD456 the protease gene was amplified from chromosomal DNA of the wild type strains or from the clones deposited as DSM16719 and DSM16722 using the primers:

```
                                (SEQ ID NO: 31)
JT169 Expression Forward
AGTTCATCGATCGGGGGAGCTAGCAGCTTCGA (SEQ ID NO: 32)
JT169 Expression Reverse
TGATTAACGCGTTTAGTTCACAATCGCCAATG (SEQ ID NO: 33)
PD456 Expression Forward
AGTTCATCGATCGGGGGGGCTAGCAACTTTGA (SEQ ID NO: 34)
PD456 Expression Reverse
TGATTAACGCGTTTAGTTCACAATCGCCAATG
```

These PCR products were digested with restriction enzymes Cla1 and Mlu1 (except AA351 that was digested with (Nar1 and Mlu1) and ligated into pDG268neo, and expressed as described in Example 2.

EXAMPLE 4

Purification and Characterisation

Purification

This procedure relates to purification of a 2 liter scale fermentation for the production of the subtilases of the invention in a *Bacillus* host cell.

Approximately 1.6 liters of fermentation broth are centrifuged at 5000 rpm for 35 minutes in 1 liter beakers. The supernatants are adjusted to pH 6.5 using 10% acetic acid and filtered on Seitz Supra® S100 filter plates.

The filtrates are concentrated to approximately 400 ml using an Amicon® $CH_2A$ UF unit equipped with an Amicon® S1Y10 UF cartridge. The UF concentrate is centrifuged and filtered prior to absorption at room temperature on a Bacitracin affinity column at pH 7. The protease is eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step are combined and applied to a 750 ml Sephadex® G25 column (5 cm dia.) equilibrated with a buffer containing 0.01 dimethylglutaric acid, 0.2 M boric acid and 0.002 m calcium chloride adjusted to pH 6.5.

Fractions with proteolytic activity from the Sephadex® G25 column are combined and applied to a 150 ml CM Sepharose® CL 6B cation exchange column (5 cm dia.) equilibrated with a buffer containing 0.01 M dimethylglutaric acid, 0.2 M boric acid, and 0.002 M calcium chloride adjusted to pH 6.5.

The protease is eluted using a linear gradient of 0-0.1 M sodium chloride in 2 liters of the same buffer.

In a final purification step subtilase containing fractions from the CM Sepharose® column are combined and concentrated in an Amicon® ultrafiltration cell equipped with a GR81PP membrane (from the Danish Sugar Factories Inc.).

EXAMPLE 5

Stability of Subtilases

The stability of the produced subtilases was evaluated in a standard Western European dishwashing tablet detergent without other enzymes than the experimentally added subtilases. The stability of the subtilases is determined as the residual proteolytic activity after incubation of the subtilase in a detergent.

The formulation of a standard Western European Tablet detergent is defined as

| Component | Percentage |
| --- | --- |
| Non ionic surfactants | 0-10% |
| Foam regulators | 1-10% |
| Bleach (per-carbonate or per-borate) | 5-15% |
| Bleach activators (e.g. TAED) | 1-5% |
| Builders (e.g. carbonate, phosphate, tri-phosphate, Zeolite) | 50-75% |
| Polymers | 0-15% |
| Perfume, dye etc. | <1% |
| Water and fillers (e.g. sodium sulphate) | Balance |

Assay for Proteolytic Activity

The proteolytic activity was determined with casein as substrate. One Casein Protease Unit (CPU) is defined as the amount of protease liberating about 1 µM of primary amino groups (determined by comparison with a serine standard) per minute under standard conditions, i.e., incubation for about 30 minutes at about 25° C. at pH 9.5.

The proteolytic activity may also be determined by measuring the specific hydrolysis of succinyl-Ala-Ala-Pro-Leu-p-nitroanilide by said protease. The substrate is initially dissolved in for example, DMSO (Dimethyl Sulfoxide) and then diluted about 50 fold in about 0.035 M borate buffer, about pH 9.45. All protease samples may be diluted about 5-10 fold by the same borate buffer. Equal volumes of the substrate solution and sample are mixed in a well of an ELISA reader plate and read at about 405 nm at 25° C. All sample activities and concentrations are normalized to the standard protease solution activity and concentration, respectively.

A typical Western European tablet detergent for automated dishwashing was dissolved (5.5 g/L) in 9° dH water at ambient temperature maximum 30 minutes prior to start of analyses. Samples of subtilases were diluted to a concentration of 2-4 CPU/ml in Britten Robinson buffer (Britten Robinson buffer is: 40 mM Phosphate, 40 mM Acetate and 40 mM Borate) pH9.5. For the analyses every sample was divided and tested under two conditions: For the control the subtilase was diluted 1:9 in Britten Robinson buffer pH9.5 to a final volume of 1 ml. This sample was analysed immediately after dilution. For the detergent stability the subtilase sample was diluted 1:9 in detergent solution (detergent concentration in the stability test is 5 g/L) these samples were incubated at 55° C. for 30 minutes prior to analysis by addition of casein substrate.

The assay was started by addition of 2 volumes of casein substrate (casein substrate was 2 g of casein (Merck, Hammerstein grade) in 100 ml of Britten Robinson buffer pH 9.5, pH was re-adjusted to 9.5 when the casein is in solution). Samples are kept isothermic at 25° C. for 30 minutes. The reaction was stopped by addition of 5 ml TCA solution (TCA solution is 89.46 g of Tri-chloric acid, 149.48 g of Sodium acetate-tri-hydrate and 94.5 ml of glacial acetic acid in 2.5 L of deionised water). The samples are incubated at ambient temperature for at least 20 minutes and filtered through Whatman® paper filter no. 42.

400 µl of filtrate is mixed with 3 ml OPA reagent (OPA reagent is composed of: 3.812 g of borax, 0.08% EtOH, 0.2% DTT and 80 mg of o-phthal-dialdehyd in 100 ml water). Absorption at 340 nM is measured and CPU is calculated from the concentration of free amines on a standard of a solution of 0.01% L-serine (Merck art. 7769).

Enzymatic proteolysis of reference proteases in the typical Western European tablet detergent:

| | CPU/L | | |
| --- | --- | --- | --- |
| Protease | Control | Detergent | % activity |
| Alcalase | 250 | 31 | 13% |
| Esperase | 220 | 116 | 53% |
| Savinase | 538 | 21 | 4% |
| Everlase16L | 2383 | 86 | 4% |
| Ovozyme | 2848 | 44 | 2% |
| BLAP-S | 36 | 1 | 3% |
| JP170 | 754 | 370 | 49% |

Enzymatic proteolysis of cloned full length proteases of the invention in the typical Western European tablet detergent:

| | CPU/L | | |
| --- | --- | --- | --- |
| Clone | Control | Detergent | % activity |
| PD456-1 | 87 | 95 | 109% |
| PD456-2 | 84 | 91 | 108% |
| PD456-3 | 85 | 93 | 109% |
| PD456-4 | 77 | 84 | 109% |
| JT169-1 | 74 | 65 | 88% |
| JT169-2 | 71 | 60 | 85% |
| JT169-3 | 62 | 59 | 95% |
| JT169-4 | 59 | 58 | 98% |

Enzymatic proteolysis of cloned hybrid proteases of the invention in the typical Western European tablet detergent. The reference is JP170:

| | CPU/I | | |
|---|---|---|---|
| Hybrid | Control | Detergent | % activity |
| JP170 | 67 | 36 | 53% |
| JP170 | 66 | 38 | 57% |
| JP75-1 | 70 | 78 | 112% |
| JP75-2 | 72 | 82 | 114% |
| JP40-1 | 67 | 79 | 118% |
| JP40-2 | 66 | 78 | 118% |
| PD456-1 | 74 | 80 | 108% |
| PD456-2 | 74 | 80 | 108% |
| JT169-1 | 83 | 79 | 95% |
| JT169-2 | 84 | 82 | 97% |

As can be seen from the results the subtilases and subtilase hybrids of the invention exhibit a greatly improved proteolytic activity after incubation in a detergent as compared to the prior art subtilase JP170. Therefore, the subtilases and subtilase hybrids of the invention exhibits improved stability in a detergent as compared to the prior art.

The invention claimed is:

1. An isolated subtilase, comprising an amino acid sequence which is at least 95% identical to the sequence of SEQ ID NO:8, and which has proteolytic activity.

2. An isolated subtilase, comprising an amino acid sequence which is at least 96% identical to the sequence of SEQ ID NO:8, and which has proteolytic activity.

3. An isolated subtilase, comprising an amino acid sequence which is at least 97% identical to the sequence of SEQ ID NO:8, and which has proteolytic activity.

4. An isolated subtilase, comprising an amino acid sequence which is at least 98% identical to the sequence of SEQ ID NO:8, and which has proteolytic activity.

5. The subtilase of claim 1, comprising an amino acid sequence which is at least 99% identical to the sequence of SEQ ID NO:8.

6. The subtilase of claim 1, which comprises the sequence of SEQ ID NO:8.

7. The subtilase of claim 1, which consists of the sequence of SEQ ID NO:8.

8. A detergent composition comprising the subtilase of claim 1 and a surfactant.

9. An isolated nucleic acid sequence encoding the subtilase of claim 1.

10. The nucleic acid sequence of claim 8 as shown in SEQ ID NO:7.

11. A nucleic acid construct comprising the nucleic acid sequence of claim 9 operably liked to one or more control sequences capable of directing the expression of the polypeptide in a suitable expression host.

12. A recombinant expression vector comprising the nucleic acid construct of claim 11, a promoter, and transcriptional and translation stop signals.

13. The vector of claim 12, further comprising a selectable marker.

14. A recombinant host cell comprising the nucleic acid construct of claim 11.

15. A method for producing a subtilase, comprising
 a) cultivating a recombinant host cell of claim 14; and
 b) recovering the subtilase.

16. A core subtilase which has an amino acid sequence which is 96% identical to the sequence of amino acids from position 49 through position 391 of SEQ ID NO:8.

17. A hybrid subtilase comprising the core sequence of claim 16.

* * * * *

UNITED STATES PATENT AND TRADEMARK OFFICE
CERTIFICATE OF CORRECTION

| | |
|---|---|
| PATENT NO. | : 8,232,087 B2 |
| APPLICATION NO. | : 13/023626 |
| DATED | : July 31, 2012 |
| INVENTOR(S) | : Nielsen et al. |

It is certified that error appears in the above-identified patent and that said Letters Patent is hereby corrected as shown below:

Title Page, item (56) References Cited

U.S. Patent Documents:

Insert -- US 2004/007232   4/2004   Sato et al. --

Item (56) References Cited

Foreign Patent Documents:

Insert -- WO 98/20115   5/1998 --

Signed and Sealed this
Eighteenth Day of September, 2012

David J. Kappos
*Director of the United States Patent and Trademark Office*